(12) United States Patent
Richard et al.

(10) Patent No.: US 9,526,924 B2
(45) Date of Patent: Dec. 27, 2016

(54) COMPOSITION COMPRISING A SCREENING AGENT OF THE LIPOPHILIC 2-HYDROXYBENZOPHENONE TYPE AND A SILICON-COMPROMISING S-TRIAZINE SUBSTITUTED BY AT LEAST TWO ALKYLAMINOBENZOATE GROUPS

(75) Inventors: Herve Richard, Gagny (FR); Florence L'Alloret, Paris (FR); Didier Candau, Bievres (FR); Cecile Fiandino, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/390,894

(22) PCT Filed: Aug. 18, 2010

(86) PCT No.: PCT/FR2010/051730
§ 371 (c)(1),
(2), (4) Date: Feb. 16, 2012

(87) PCT Pub. No.: WO2011/023886
PCT Pub. Date: Mar. 3, 2011

(65) Prior Publication Data
US 2012/0201767 A1    Aug. 9, 2012

Related U.S. Application Data

(60) Provisional application No. 61/272,261, filed on Sep. 4, 2009, provisional application No. 61/272,260, filed on Sep. 4, 2009.

(30) Foreign Application Priority Data

Aug. 28, 2009 (FR) ..................................... 09 55882
Aug. 28, 2009 (FR) ..................................... 09 55883

(51) Int. Cl.
  *A61K 8/58* (2006.01)
  *A61Q 17/04* (2006.01)
  *A61K 8/35* (2006.01)
  *A61K 8/41* (2006.01)
  *A61K 8/49* (2006.01)

(52) U.S. Cl.
  CPC ............. *A61Q 17/04* (2013.01); *A61K 8/35* (2013.01); *A61K 8/415* (2013.01); *A61K 8/494* (2013.01); *A61K 8/585* (2013.01)

(58) Field of Classification Search
  CPC .................................. A61K 8/58; A61Q 17/04
  See application file for complete search history.

(56) References Cited

U.S. PATENT DOCUMENTS

| | | | |
|---|---|---|---|
| 6,517,742 B1 * | 2/2003 | Richard | A61K 8/585 252/401 |
| 6,699,461 B2 * | 3/2004 | Candau | 424/59 |
| 2003/0129152 A1 * | 7/2003 | Candau | A61K 8/35 424/59 |
| 2003/0161793 A1 | 8/2003 | Candau | |
| 2008/0138303 A1 * | 6/2008 | Candau et al. | 424/59 |
| 2008/0145324 A1 * | 6/2008 | Richard et al. | 424/59 |

FOREIGN PATENT DOCUMENTS

| | | |
|---|---|---|
| EP | 0843996 A2 | 5/1998 |
| EP | 0864313 A2 | 9/1998 |
| EP | 1 046 391 A2 | 10/2000 |
| FR | 2886143 A1 | 12/2006 |
| JP | 2003-192559 A | 7/2003 |
| JP | 2008-545728 A | 12/2008 |
| JP | 2009-520745 A | 5/2009 |
| WO | WO-2006/128732 A1 | 12/2006 |
| WO | WO-2007/071584 A2 | 6/2007 |

OTHER PUBLICATIONS

Office Action from the Japanese Patent Office issued in Japanese Application No. 2012-526098, dated Jul. 28, 2014.

* cited by examiner

*Primary Examiner* — Ileana Popa
*Assistant Examiner* — Nicole Babson
(74) *Attorney, Agent, or Firm* — Polsinelli PC

(57) ABSTRACT

The present invention relates to a composition comprising, in a cosmetically acceptable carrier, at least one UV screening system, characterized in that it comprises:
(i) at least one screening agent of lipophilic hydroxybenzophenone type; and
(ii) at least one silicon-comprising s-triazine of formula (III) substituted by at least two alkylaminobenzoate groups.

In some embodiments, the composition also includes:
(iii) a dibenzoylmethane derivative.

17 Claims, No Drawings

COMPOSITION COMPRISING A SCREENING AGENT OF THE LIPOPHILIC 2-HYDROXYBENZOPHENONE TYPE AND A SILICON-COMPROMISING S-TRIAZINE SUBSTITUTED BY AT LEAST TWO ALKYLAMINOBENZOATE GROUPS

CROSS REFERENCE TO RELATED APPLICATIONS

This application is a 35 U.S.C. 371 National Stage application of International Application No. PCT/FR2010/051730, filed Aug. 18, 2010, which application claims priority to French Application No. 0955882, filed Aug. 28, 2009; French Application No. 0955883, filed Aug. 28, 2009; U.S. Provisional Application No. 61/272,261, filed Sep. 4, 2009; and U.S. Provisional Application No. 61/272,260, filed Sep. 4, 2009, the entire contents of each which are incorporated herein by reference.

STATEMENT REGARDING FEDERALLY SPONSORED RESEARCH OR DEVELOPMENT

Not Applicable

THE NAMES OF PARTIES TO A JOINT RESEARCH AGREEMNT

Not Applicable

INCORPORATION BY REFERENCE OF MATERIAL SUBMITTED ON A COMPACT DISC

Not Applicable

BACKGROUND OF THE DISCLOSURE

1. Field of the Disclosure

The present invention relates to a composition comprising, in a cosmetically acceptable carrier, at least one UV screening system, characterized in that it comprises:
(i) at least one screening agent of lipophilic 2-hydroxybenzophenone type;
(ii) at least one silicon-comprising s-triazine of formula (III) substituted by at least two alkylaminobenzoate groups.

2. Description of Related Art

It is known that light radiation with wavelengths of between 280 nm and 400 nm makes possible burning of the human epidermis and that rays with wavelengths more particularly of between 280 and 320 nm, known under the name of UV-B, cause erythemas and skin burns which may be harmful to the development of natural tanning. For these reasons, and also for aesthetic reasons, there is constant demand for means for controlling this natural tanning in order thus to control the colour of the skin; this UV-B radiation should thus be screened out.

It is also known that UV-A rays, with wavelengths between 320 and 400 nm, which cause browning of the skin, are liable to induce adverse changes therein, in particular in the case of sensitive skin or skin that is continually exposed to solar radiation. UV-A rays cause in particular a loss of elasticity of the skin and the appearance of wrinkles leading to premature ageing of the skin. They promote triggering of the erythemal reaction or amplify this reaction in certain individuals and may even be the cause of phototoxic or photoallergic reactions. Thus, for aesthetic and cosmetic reasons, for instance conservation of the skin's natural elasticity, for example, people increasingly wish to control the effect of UV-A rays on their skin. It is thus desirable also to screen out UV-A radiation.

For the purpose of protecting the skin and keratin materials against UV radiation, antisun compositions comprising organic screening agents that are active in the UV-A range and in the UV-B range are generally used.

Lipophilic benzophenone derivatives are known to be photostable screening agents which absorb UV-A radiation and some of them, such as amino-substituted 2-hydroxybenzophenones, such as n-hexyl 2-(4-diethylamino-2-hydroxybenzoyl)benzoate, sold under the name Uvinul A+ by BASF, are highly effective.

UV-B screening agents which are particularly advantageous and which are widely used at the present time are lipophilic screening agents of the silicon-free 1,3,5-triazine type. They are described in Patent Applications EP-A-0 517 104, EP-A-0 570 838, EP-A-796 851 and EP-A-0 775 698. The derivative 2,4,6-tris[p-(2'-ethylhexyl-1'-oxycarbonyl)anilino]-1,3,5-triazine, sold in particular under the trade name "Uvinul T150" by BASF, is known in particular. These lipophilic screening agents active in the UV-B region exhibit the disadvantage of being solid at ambient temperature. Their use in antisun compositions brings about formulation restrictions, with a need to identify solvents which make it possible to correctly dissolve them.

Other advantageous UV-B screening agents used in antisun compositions at the present time are alkyl β,β-diphenylacrylate or alkyl α-cyano-β,β-diphenylacrylate; mention may be made of 2-ethylhexyl α-cyano-β,β-diphenylacrylate, also known as octocrylene. It is available commercially and is sold in particular under the name "UVINUL N 539" by BASF. These screening agents exhibit the advantage of being easy to formulate but their screening properties are relatively weak, which is reflected by high concentrations of use in order to obtain an advantageous level of UV screening.

Cinnamic derivatives, such as 2-ethylhexyl 4-methoxycinnamate or isoamyl 4-methoxycinnamate, are good solvents for UV screening agents which are difficult to dissolve in oils and exhibit good photoprotection properties in the UV-B region. These cinnamic derivatives have the disadvantage of exhibiting an inadequate photostability and of disrupting the photostability of the complete screening systems into which they are introduced.

Silicon-comprising s-triazines substituted by at least two alkylaminobenzoate or alkylaminobenzamide groups are known, in Applications EP 0 841 341 and EP 1 891 079, for their absorbing properties in the UV-B region. The Applicant Company, during its research studies, has found that not all of these silicon-comprising triazine compounds substituted by at least two alkylaminobenzoate groups, in particular those for which the alkyl chain comprises more than 10 carbon atoms, make it possible to obtain a satisfactory effectiveness in combination with UV-A screening agents.

It thus appears necessary to have available a system which extensively screens out UV-A and UV-B radiation and which is easy to employ in antisun compositions without the abovementioned disadvantages, namely to obtain a system which screens out UV-A and UV-B rays which is photostable, which has a high protection factor and which has good solubility in antisun formulations.

In point of fact, the Applicant Company has now just discovered, surprisingly, that, by combining at least one screening agent of lipophilic 2-hydroxybenzophenone type with a silicon-comprising s-triazine substituted by at least two alkylaminobenzoate groups of formula (III), the definition of which will be given later, it is possible to obtain a system which extensively screens out UV-A and UV-B radiation, and which is easy to employ in antisun compositions without the abovementioned disadvantages.

This discovery forms the basis of the present invention.

BRIEF SUMMARY OF THE DISCLOSURE

In accordance with one of the subject-matters of the present invention, a composition is now proposed comprising, in a cosmetically acceptable carrier, at least one UV screening system, characterized in that it comprises:
(i) at least one lipophilic screening agent of hydroxybenzophenone type;
(ii) at least one silicon-comprising s-triazine of formula (III) substituted by at least two alkylaminobenzoate groups.

Other characteristics, aspects and advantages of the invention will become apparent on reading the detailed description which will follow.

BRIEF SUMMARY OF THE DRAWINGS

Not Applicable

DETAILED DESCRIPTION OF THE DISCLOSURE

The term "cosmetically acceptable" means compatible with the skin and/or its integuments, which has a pleasant colour, odour and feel, and which does not cause any unacceptable discomfort (stinging, tautness or redness) liable to dissuade the consumer from using this composition.

The term "lipophilic compound" means any cosmetic or dermatological compound capable of being completely dissolved in the molecular state in a liquid fatty phase or else of being dissolved in the colloidal form (for example in the micelle form) in a liquid fatty phase.

The Applicant Company has also discovered, surprisingly, that the use of a screening agent active in the UV-B region of the type consisting of silicon-comprising s-triazine substituted by two aminobenzoate groups of formula (III), which will be defined in detail later, in combination with a UV-A screening agent of lipophilic 2-hydroxybenzophenone type, in the presence of a dibenzoylmethane derivative, makes it possible to obtain good photostabilization of the dibenzoylmethane derivatives with regard to UV radiation, in association with good effectiveness of protection in the UV-B region, in order to be able to ensure complete and effective protection of the skin from attacks related to exposure to UV radiation constitutes, at the present time, a problem which has still not been solved in an entirely satisfactory fashion.

This is because dibenzoylmethane derivatives, in particular 4-tert-butyl-4'-methoxydibenzoylmethane, are known as screening agents active in the UV-A region and are described in particular in French Patent Applications FR-A-2 326 405 and FR-A-2 440 933 and in European Patent Application EP-A-0 114 607. Unfortunately, it transpires that dibenzoylmethane derivatives are products which are relatively sensitive to ultraviolet radiation (in particular UV-A radiation), that is to say that they decompose more or less rapidly under the action of the latter. Thus, this substantial lack of photochemical stability in the face of the ultraviolet radiation to which they are by nature intended to be subjected does not make it possible to guarantee continual protection during prolonged exposure to the sun.

Several means are known at the present time for the photostabilization of dibenzoylmethane derivatives. Thus, it is known, in Patent Application EP 0 514 491, that alkyl $\beta,\beta$-diphenylacrylate or $\alpha$-cyano $\beta,\beta$-diphenylacrylate derivatives substantially improve the photostability of dibenzoylmethane derivatives. Unfortunately, while these screening agents are very effective with regard to the improvement in the photostability of dibenzoylmethane derivatives, they still exhibit a mediocre absorbing power for UV-B radiation.

It is also known, in Patent Application EP 1 280 505, that Bis-Ethylhexyloxyphenol Methoxyphenyl Triazine alone improves the photostability of dibenzoylmethane derivatives. Unfortunately, while this screening agent has a high absorbing power for UV-B radiation, it nevertheless exhibits a limited effectiveness with regard to the improvement in the photostability of dibenzoylmethane derivatives and also limited solubility in oils.

Provision has also been made, in Applications EP 0 843 996 and EP 0 864 313, to improve the photostability of a dibenzoylmethane derivative with a lipophilic 2-hydroxybenzophenone, such as 2-hydroxy-4-methoxybenzophenone or benzophenone-3. This combination does not make it possible to obtain a photostability of the dibenzoylmethane which is completely satisfactory or to obtain broad coverage of the UV spectrum.

Patent Applications EP 1 323 411 and U.S. Pat. No. 6,699,461, which describe antisun compositions comprising an amino-substituted 2-hydroxybenzophenone derivative in combination with a dibenzoylmethane derivative in a ratio by weight of the amino-substituted 2-hydroxybenzophenone derivative to the dibenzoylmethane derivative of greater than 1, are also known. Unfortunately, while this combination has an improved photostability, it is found to be highly restricted to the ratio of the two screening agents and does not make it possible to obtain broad coverage of the UV spectrum.

Provision has also been made, in Application EP 1 891 079, to improve the photostability of dibenzoylmethane derivatives with silicon-comprising s-triazines substituted by at least two alkylaminobenzoate or alkylaminobenzamide groups. The Applicant Company, during its research studies, has found that not all of these silicon-comprising triazine compounds, in particular those having alkylaminobenzoate groups whose alkyl chain comprises more than 10 carbon atoms, make it possible to obtain a satisfactory effectiveness.

In point of fact, the Applicant Company has now just discovered, surprisingly, that the use of a screening agent active in the UV-B region of the type consisting of silicon-comprising s-triazine substituted by two aminobenzoate groups of formula (III), which will be defined in detail later, in combination with a UV-A screening agent of lipophilic 2-hydroxybenzophenone type, in the presence of a dibenzoylmethane derivative, makes it possible to solve the abovementioned technical problems.

Thus, in accordance with one of the subject-matters of the present invention, a composition is now proposed comprising, in a cosmetically acceptable carrier, at least one UV screening system, characterized in that it comprises:
(i) at least one dibenzoylmethane derivative;
(ii) at least one UV screening agent of lipophilic 2-hydroxybenzophenone type; and
(iii) at least one silicon-comprising s-triazine substituted by at least two alkylaminobenzoate groups of formula (III).

It also relates to a method for the photostabilization with regard to radiation of at least one screening agent of the type derived from dibenzoylmethane by an effective amount of at least one screening agent of lipophilic 2-hydroxybenzophenone type and of at least one silicon-comprising s-triazine substituted by at least two aminobenzoate groups of formula (III) defined below.

The term "effective amount" means an amount sufficient to obtain a noteworthy and significant improvement in the photostability of the dibenzoylmethane derivative or derivatives in the cosmetic composition. This minimum amount of lipophilic 2-hydroxybenzophenone and silicon-comprising s-triazine of formula (III), which can vary according to the nature of the carrier selected for the composition, can be determined without any difficulty by means of a conventional test for measuring photostability, such as that given in the examples below.

2-Hydroxybenzophenone Screening Agents

Mention may be made, among screening agents of the 2-hydroxybenzophenone type, of:

2,4-dihydroxybenzophenone with the INCI name: benzophenone-1, sold under the trade name "Uvinul 400" by BASF, 2,2',4,4'-tetrahydroxybenzophenone with the INCI name: benzophenone-2, sold under the trade name "Uvinul D50" by BASF 2-hydroxy-4-methoxybenzophenone with the INCI name: benzophenone-3 or oxybenzone, sold under the trade name "Uvinul M40" by BASF, 2,2'-dihydroxy-4,4'-dimethoxybenzophenone with the INCI name: benzophenone-6, sold under the trade name "Helisorb 11" by Norquay, 2,2'-dihydroxy-4-methoxybenzophenone with the INCI name: benzophenone-8 sold under the trade name "Spectra-Sorb UV-24" by American Cyanamid, 2-hydroxy-4-methoxy-4'-methylbenzophenone with the INCI name: benzophenone-10, 2-hydroxy-4-(octyloxy)benzophenone with the INCI name: benzophenone-12.

According to a particularly preferred form of the invention, use will more particularly be made of the amino-substituted 2-hydroxybenzophenone compounds of following formula (I):

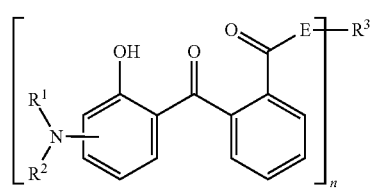

in which:

$R^1$ and $R^2$, which are identical or different, denote a $C_1$-$C_{20}$ alkyl radical, a $C_2$-$C_{20}$ alkenyl, a $C_3$-$C_{10}$ cycloalkyl or a $C_3$-$C_{10}$ cycloalkenyl or form, with the nitrogen atom to which they are bonded, a 5- or 6-membered ring;

n is a number ranging from 1 to 4;

when n=1, $R^3$ denotes a $C_1$-$C_{20}$ alkyl or alkenyl radical, a $C_1$-$C_5$ hydroxyalkyl, a $C_6$-$C_{12}$ cyclohexyl or a phenyl which can be substituted by O, N or S, aminocarbonyl or $C_1$-$C_5$ alkylcarbonyl;

when n=2, $R^3$ denotes an alkyl diradical, a cycloalkyl diradical, an alkenyl diradical or an aryl diradical or $R^3$ with E forms a diradical of formula (II):

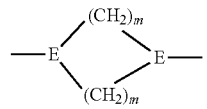

with m a number ranging from 1 to 3;
when n=3, $R^3$ is an alkyl triradical;
when n=4, $R^3$ is an alkyl tetraradical;
E is —O— or —N($R^4$)—;
$R^4$ is hydrogen or a $C_1$-$C_5$ alkyl or $C_1$-$C_5$ hydroxyalkyl radical.

Mention may be made, as $C_1$-$C_{20}$ alkyl radicals, for example of: methyl, ethyl, n-propyl, 1-methylethyl, n-butyl, 1-methylpropyl, 2-methylpropyl, 1,1-dimethyl-ethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Mention may be made, as $C_3$-$C_{10}$ cycloalkyl radicals, for example, of: cyclopropyl, cyclobutyl, cyclopentyl, cyclohexyl, cycloheptyl, 1-methylcyclo-propyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

Mention may be made, as $C_3$-$C_{10}$ cycloalkenyl radicals having one or more double bonds, of: cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

Mention may in particular be made, as examples of a 5- or 6-membered ring formed by the $R^1$ and $R^2$ radicals with the nitrogen atom, of pyrrolidine or piperidine.

A compound of formula (I) with n=1 which is very particularly preferred is n-hexyl 2-(4-diethylamino-2-hydroxybenzoyl)benzoate of formula (a):

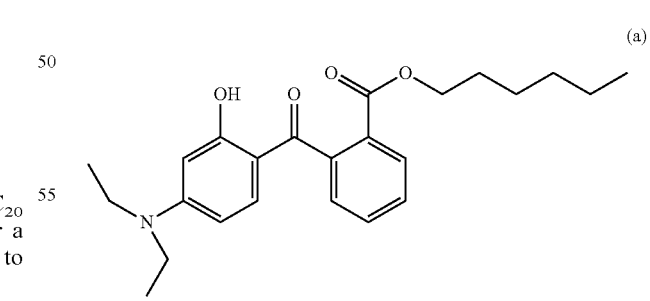

which product is sold under the trade name "Uvinul A+ by BASF.

A compound of formula (I) with n=2 which is very particularly preferred is the (2-{4-[2-(4-diethylamino-2-hydroxybenzoyl)benzoyl]piperazine-1-carbonyl}-phenyl)(4-diethylamino-2-hydroxyphenyl)methanone derivative of formula (b):

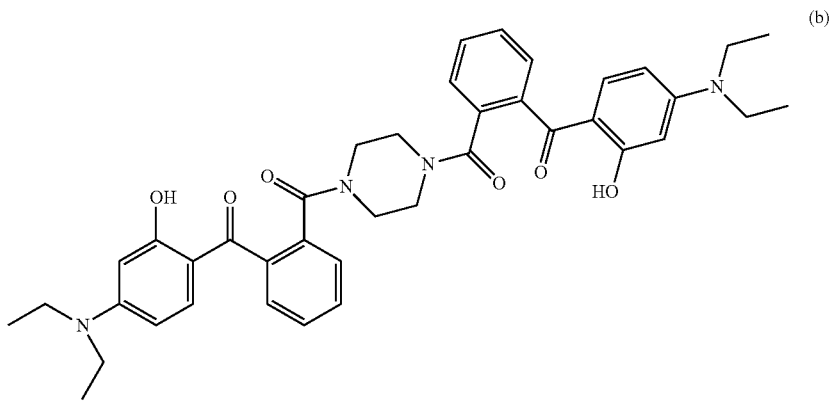 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

which product is described in Patent Application WO 2007/071584.

The compounds of formula (I) as defined above are known per se and their structures and their syntheses are described in Patent Applications EP-A-1 046 391, EP 1 133 980, DE10012408 and WO 2007/071584.

The lipophilic 2-hydroxybenzophenone screening agent or agents can be present in the compositions in accordance with the invention at contents which preferably vary from 0.01 to 10% by weight and more preferably from 0.1 to 6% by weight, with respect to the total weight of the composition.

Silicon-Comprising S-Triazine Screening Agents

The silicon-comprising s-triazine compounds in accordance with the present invention correspond to the following general formula (III) or one of its tautomeric forms:

in which:
R, which are identical or different, represent a $C_1$-$C_2$ alkyl radical, a phenyl radical, a $C_1$-$C_2$ alkoxy radical, a hydroxyl radical or the trimethylsilyloxy group;
a'=1 to 3;
the (D) group denotes an s-triazine compound of following formula (IV):

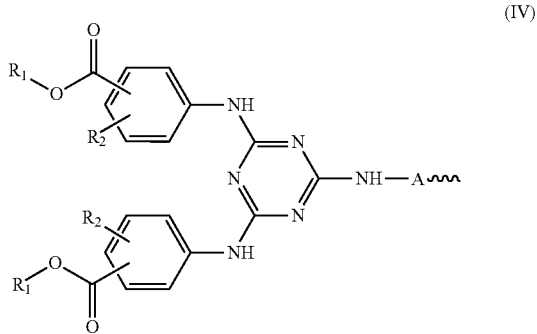

where:
$R_1$, which are identical or different, represent a linear or branched and optionally unsaturated $C_1$-$C_{10}$ alkyl radical which can comprise a $C_5$-$C_6$ cycloalkyl group,
it being possible for the (C=O)O$R_1$ group to be in the ortho, meta or para position with respect to the amino group,
$R_2$, which are identical or different, represent hydrogen, a hydroxyl radical, a linear or branched $C_1$-$C_4$ alkyl radical or a methoxy radical,
A is a divalent radical chosen from methylene or a group corresponding to one of the following formulae (V), (VI), (VII) and (VIII):

in which:
Z is a $C_1$-$C_3$ alkylene diradical,
W represents a hydrogen atom, a hydroxyl radical or a $C_1$-$C_3$ alkyl radical; in addition to the units of formula -A-(Si)(R)$_a$(O)$_{(3-a')/2}$, the organosiloxane can comprise units of formula (R)$_b$—(Si)(O)$_{(4-b)/2}$ in which
R has the same meaning as in the formula (III) and b=1, 2 or 3.

It should be noted that the derivatives of formula (III) can be used in their tautomeric forms and more particularly in the tautomeric form of following formula (III'):

in which the (D') group denotes an s-triazine compound of following formula (IV'):

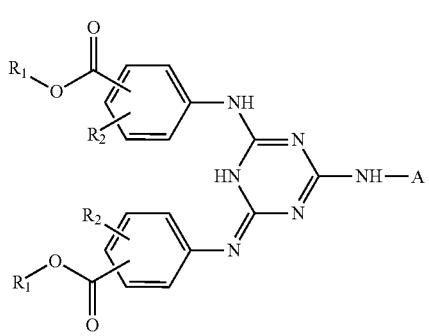

(IV')

In the formulae (III) and (III') as defined above, the alkyl radicals can be linear or branched and can be chosen in particular from the methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The alkyl radical which is particularly preferred is the butyl radical.

The preferred s-triazine derivatives are those for which, in the formula (III) or (III'), at least one and more preferably still all of the following characteristics are fulfilled:

R is methyl,
a'=1 or 2,
$R_1$ is a $C_4$-$C_8$ radical,
Z=—$CH_2$—,
W=H.

Preferably, the s-triazine compounds of the invention are represented by the following formulae (IIIa) and (IIIb):

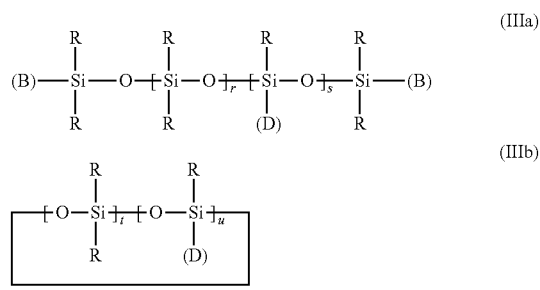

in which:
(D) corresponds to the formula (III) as defined above,
R has the same definition as in the formula (II),
(B), which are identical or different, are chosen from the R radical and the (D) radical,
r is an integer between 0 and 20 inclusive,
s is an integer ranging from 0 to 5 and, if s=0, at least one of the two (B) symbols denotes (D),
u is an integer ranging from 1 to 5,
t is an integer ranging from 0 to 5, it being understood that t+u is equal to or greater than 3, and their tautomeric forms.

The linear diorganosiloxanes of formula (IIIa) are particularly preferred.

The linear or cyclic diorganosiloxanes of formula (IIIa) or (IIIb) coming within the scope of the present invention are random oligomers preferably exhibiting at least one and more preferably still all of the following characteristics:

R is the methyl radical, the $C_1$-$C_2$ alkoxy radical or the hydroxyl radical,
B is preferably methyl (case of the linear compounds of formula (IIIa)).

Mention will be made, as examples of compounds of formula (I) which are particularly preferred, of the following compounds of formulae (1) to (22) and their tautomeric forms:

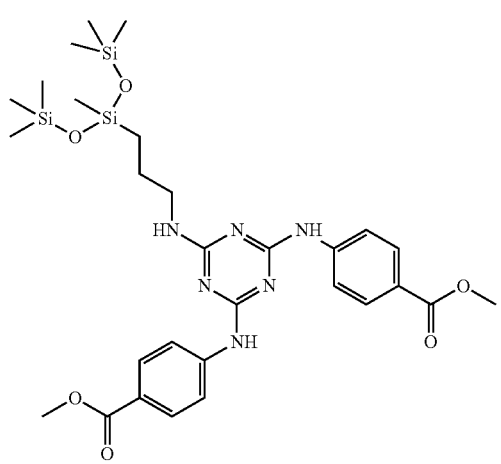

(1)

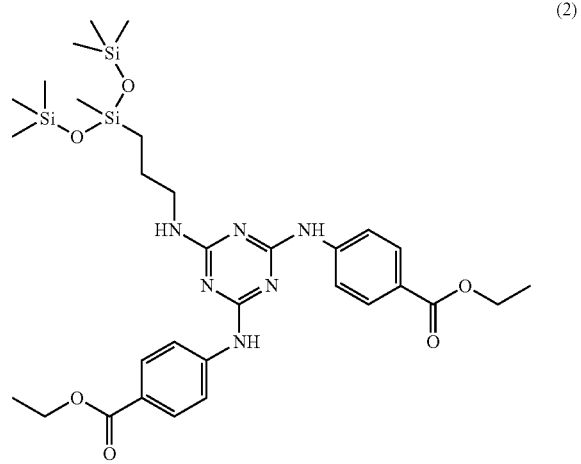

(2)

-continued
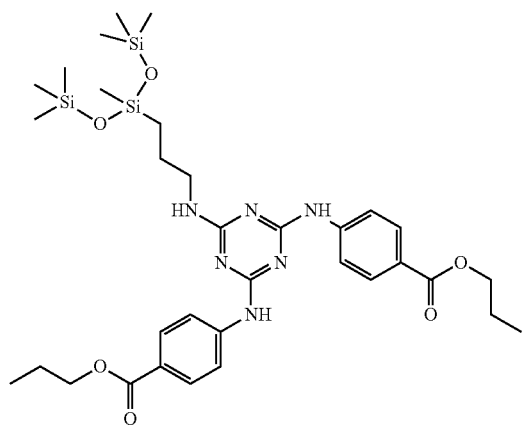
(3)
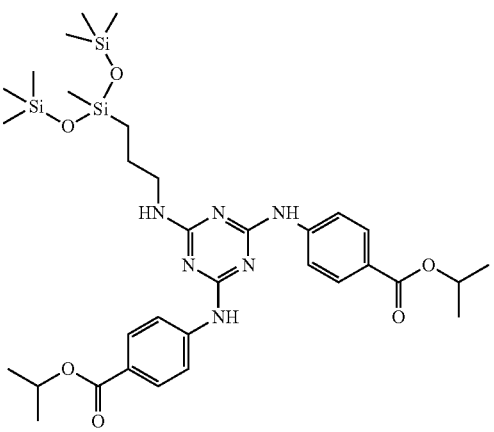
(4)
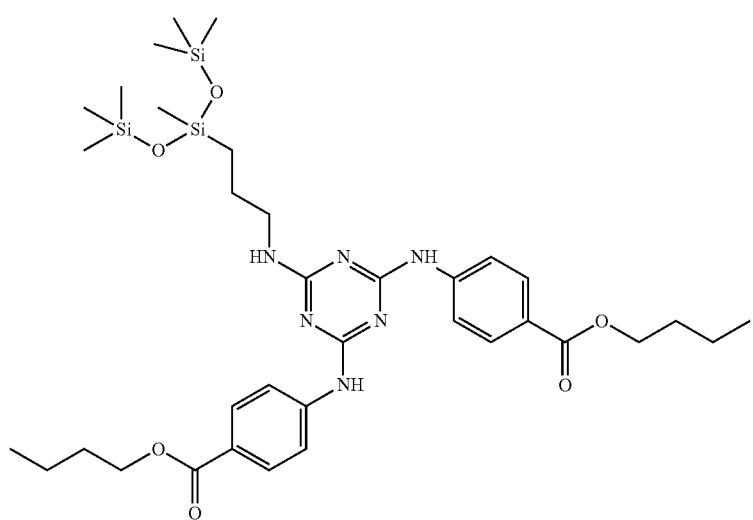
(5)
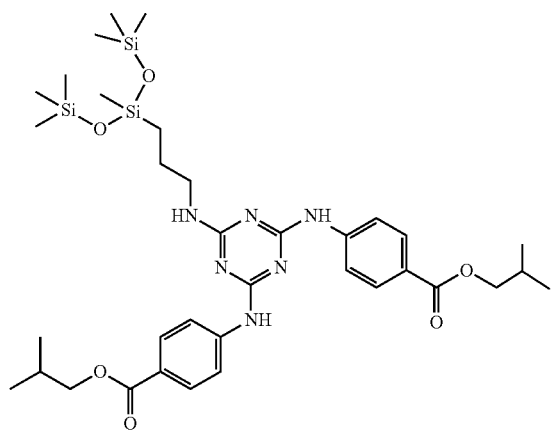
(6)
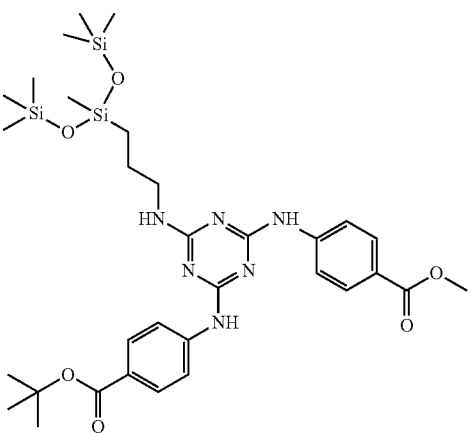
(7)

-continued
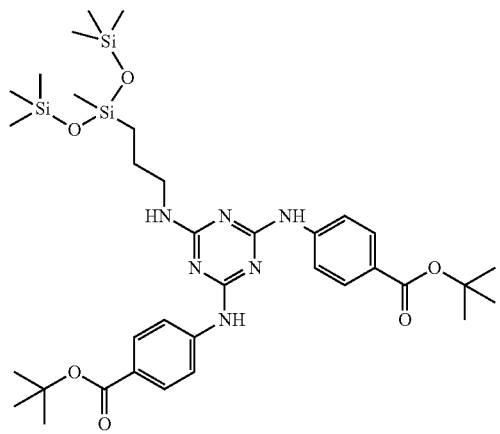
(8)
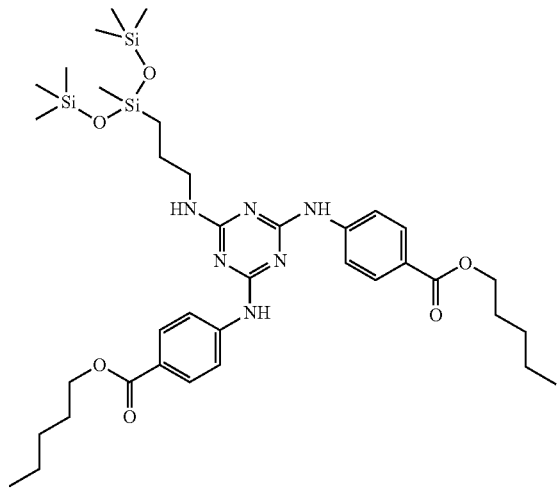
(9)
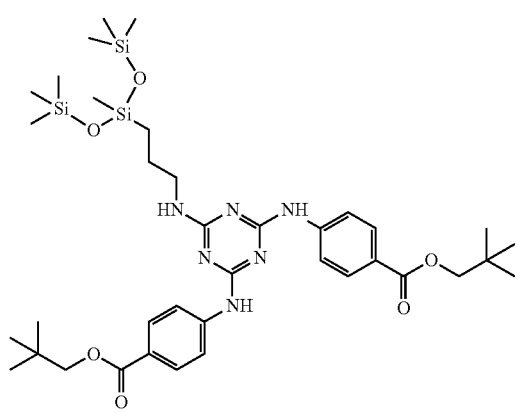
(10)
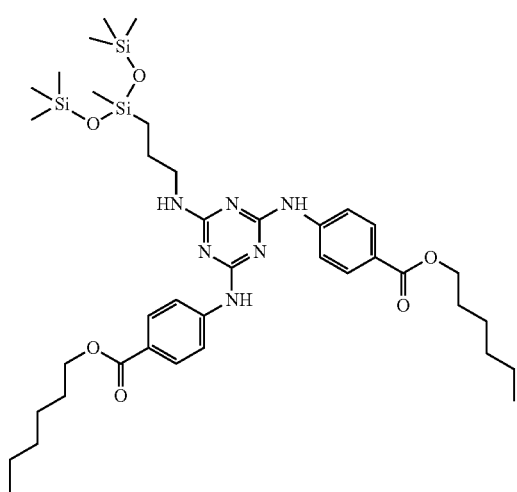
(11)
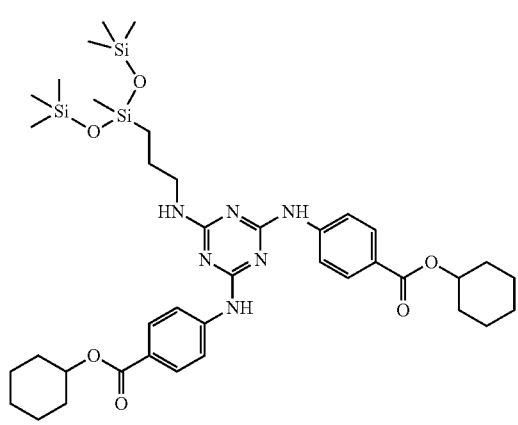
(12)
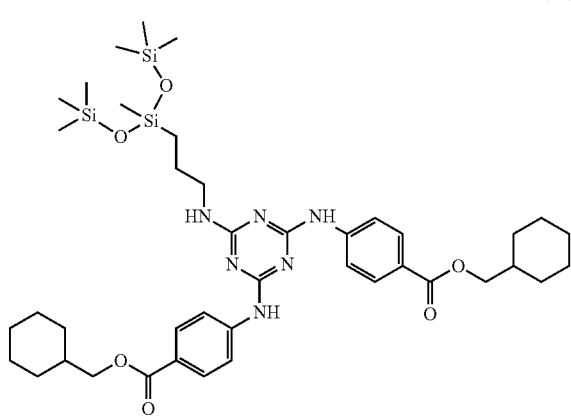
(13)

(14)
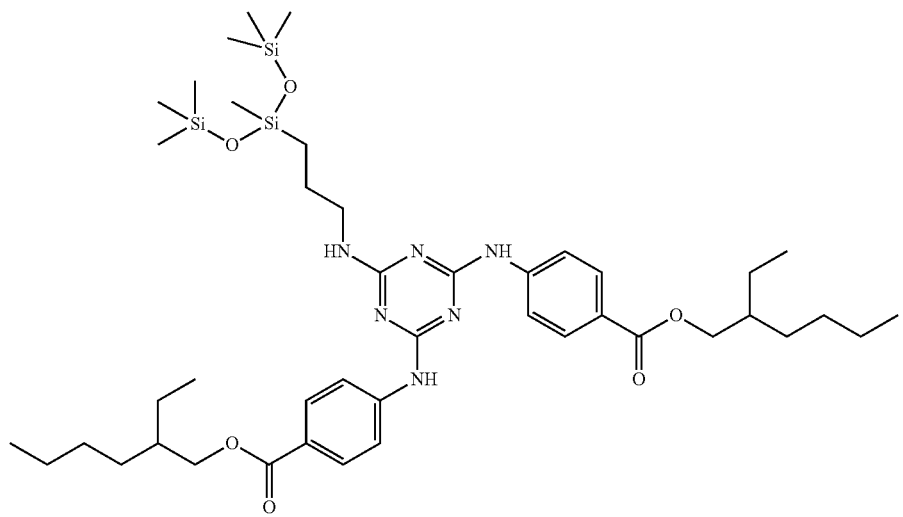
(15)
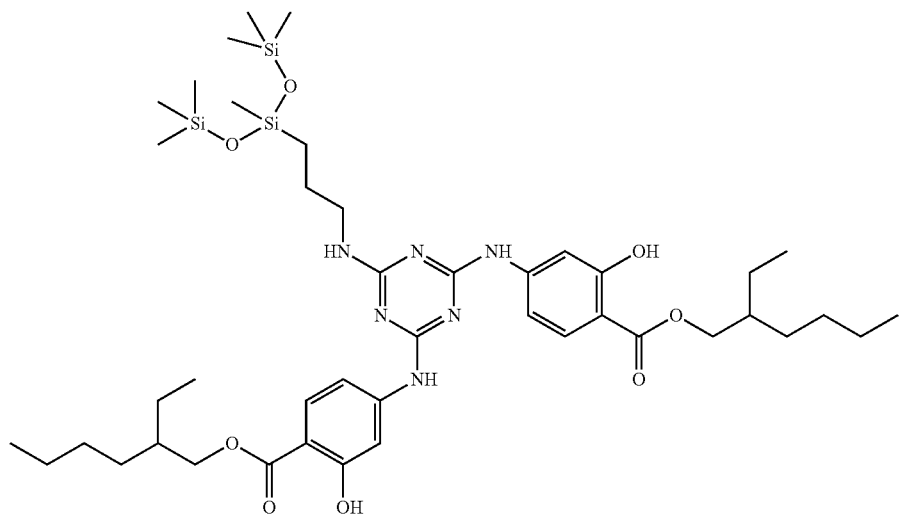
(16)
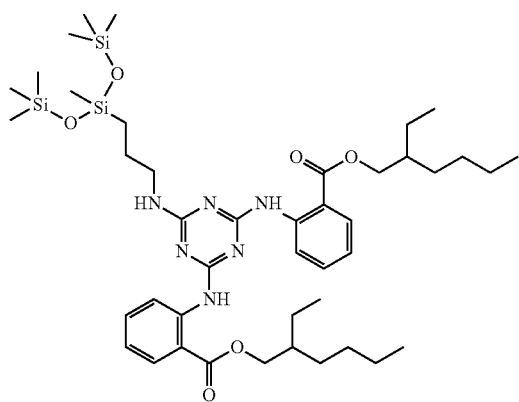
(17)
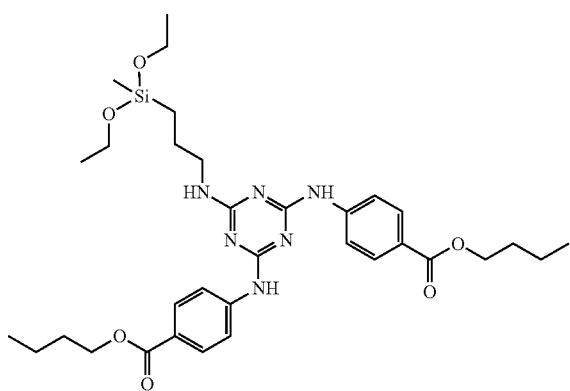

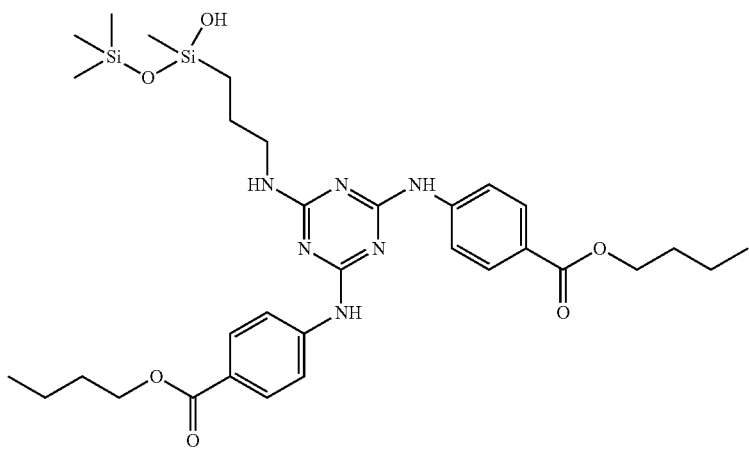
(18)
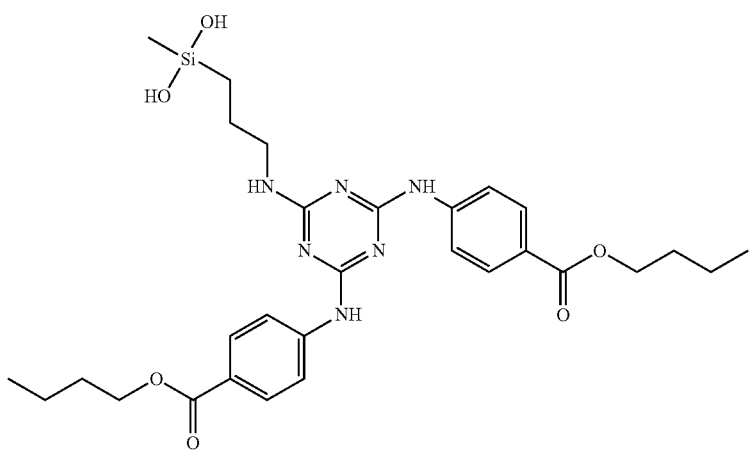
(19)
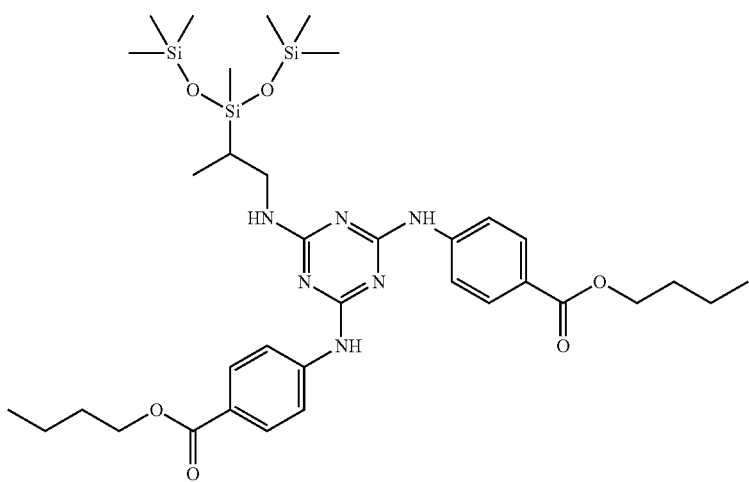
(20)

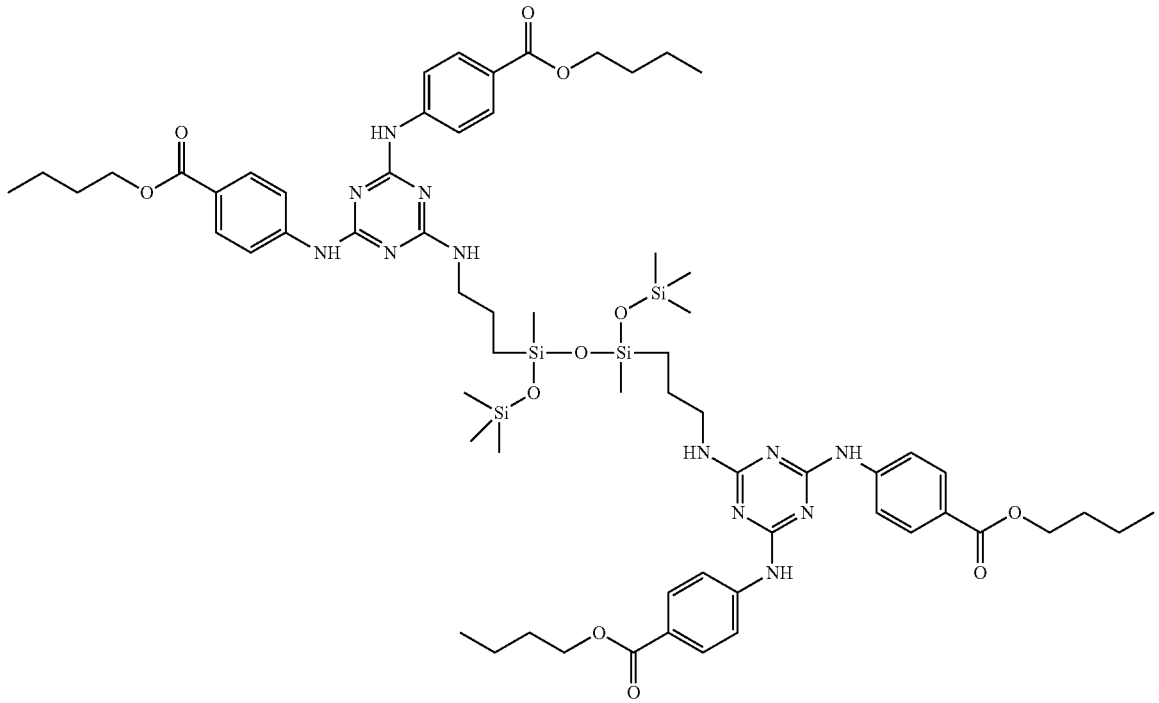

(21)

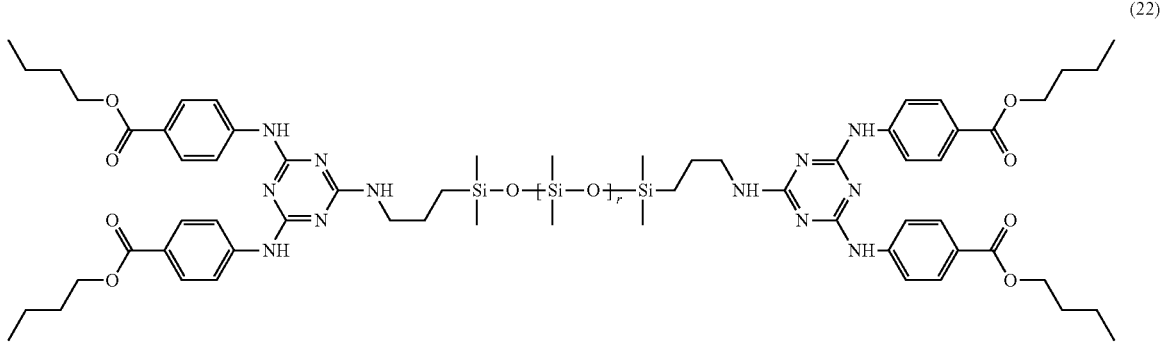

r stat = 8.1

(22)

Use will more particularly be made of the compounds such as 2,4-bis(ethyl 4'-aminobenzoate)-6-[(3-{1,3,3,3-tetramethyl-1-[(trimethylsilyl)oxy]disiloxanyl}-propyl)amino]-s-triazine of formula (2), 2,4-bis(isopropyl 4'-aminobenzoate)-6-[(3-{1,3,3,3-tetramethyl-1-[(trimethylsilyl)oxy]disiloxanyl}propyl)amino]-s-triazine of formula (4), 2,4-bis(n-butyl 4'-aminobenzoate)-6-[(3-{1,3,3,3-tetramethyl-1-[(trimethylsilyl)oxy]disiloxanyl}propyl)amino]-s-triazine of formula (5), 2,4-bis(isobutyl 4'-aminobenzoate)-6-[(3-{1,3,3,3-tetramethyl-1-[(trimethylsilyl)-oxy]disiloxanyl}propyl)amino]-s-triazine of formula (6) and 2,4-bis(neopentyl 4'-aminobenzoate)-6-[(3-{1,3,3,3-tetramethyl-1-[(trimethylsilyl)oxy]disiloxanyl}-propyl)amino]-s-triazine of formula (10).

Use will more particularly still be made of 2,4-bis(n-butyl 4'-aminobenzoate)-6-[(3-{1,3,3,3-tetramethyl-1-[(trimethylsilyl)oxy]disiloxanyl}propyl)amino]-s-triazine of formula (5):

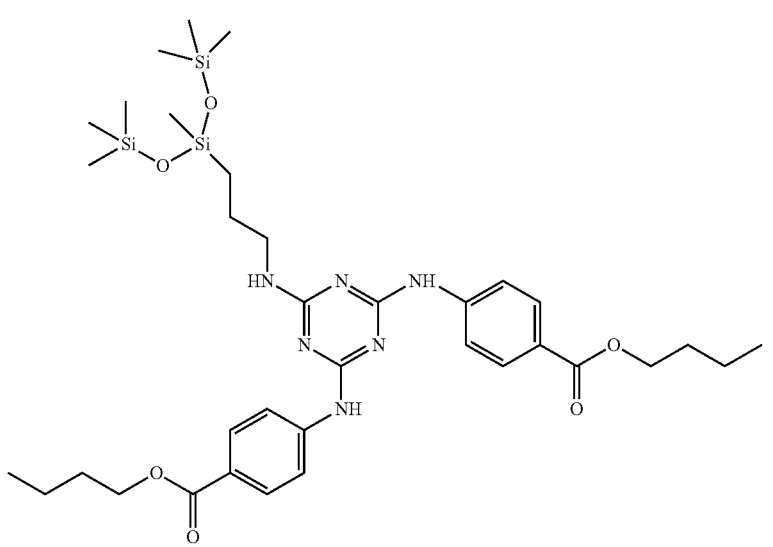

(5)

Among the compounds of formula (III) and their tautomeric forms, some are known and have been described in Patents EP 0 841 341 and FR 2 886 143. Among the compounds of formula (III) and their tautomeric forms, the products of formulae (1), (3), (4), (7), (8), (9), (10), (11), (12) and (13) are novel.

The triazine derivatives of formula (III) in accordance with the invention are preferably present in the compositions in accordance with the invention at contents of from 0.01 to 20% by weight, more preferably from 0.1 to 10% by weight and more preferably still from 0.1 to 6% by weight, with respect to the total weight of the composition.

The invention also relates to a composition comprising, in a cosmetically acceptable carrier, at least one UV screening system, characterized in that it comprises:
(i) at least one dibenzoylmethane derivative;
(ii) at least one UV screening agent of lipophilic 2-hydroxybenzophenone type; and
(iii) at least one silicon-comprising s-triazine substituted by at least two alkylaminobenzoate groups of formula (III).

It also relates to a method for the photostabilization with regard to radiation of at least one screening agent of the type derived from dibenzoylmethane by an effective amount of at least one screening agent of lipophilic 2-hydroxybenzophenone type and of at least one silicon-comprising s-triazine substituted by at least two aminobenzoate groups of formula (III) defined below.

Dibenzoylmethane Derivatives

Among the dibenzoylmethane derivatives that may especially be mentioned, in a non-limiting manner, are:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane.

Use will very particularly be made, among the dibenzoylmethane derivatives mentioned above, of 4-(tert-butyl)-4'-methoxydibenzoylmethane or Butyl Methoxy Dibenzoylmethane, provided for sale under the trade name "Parsol 1789" by DSM Nutritional Products; this screening agent corresponds to the following formula:

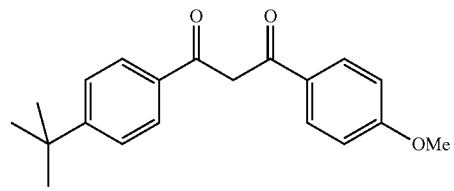 [SMILES: COc1ccc(C(=O)CC(=O)c2ccc(C(C)(C)C)cc2)cc1]

The dibenzoylmethane derivative or derivatives can be present in the compositions in accordance with the invention at contents which preferably vary from 0.01 to 10% by weight and more preferably from 0.1 to 6% by weight, with respect to the total weight of the composition.

The compositions in accordance with the invention can additionally comprise other complementary organic or inorganic UV screening agents which are active in the UV-A and/or UV-B regions and which are water-soluble or liposoluble or else insoluble in the cosmetic solvents currently used.

Of course, a person skilled in the art will take care to choose the optional additional screening agent or agents and/or their amounts so that the advantageous properties intrinsically attached to the compositions in accordance with the invention are not, or not substantially, detrimentally affected by the envisaged addition or additions.

The additional organic screening agents are chosen in particular from anthranilates; cinnamic derivatives; salicylic derivatives; camphor derivatives; β,β-diphenylacrylate derivatives; triazine derivatives other than those of formula (III); benzotriazole derivatives; benzalmalonate derivatives, in particular those mentioned in U.S. Pat. No. 5,624,663; benzimidazole derivatives; imidazolines; bis-benzazolyl derivatives, such as described in Patents EP 669 323 and U.S. Pat. No. 2,463,264; p-aminobenzoic acid (PABA) derivatives; methylenebis(hydroxyphenylbenzotriazole) derivatives, such as described in applications U.S. Pat. No. 5,237,071, U.S. Pat. No. 5,166,355, GB 2 303 549, DE 197 26 184 and EP 893 119; benzoxazole derivatives, such as described in Patent Applications EP 0 832 642, EP 1 027 883, EP 1 300 137 and DE10162844; screening polymers and screening silicones, such as those described in particular in Application WO 93/04665; dimers derived from α-alkylstyrene, such as those described in Patent Application DE19855649; or 4,4-diarylbutadienes, such as described in Applications EP 0 967 200, DE19746654, DE19755649, EP-A-1 008 586, EP 1 133 980 and EP 133 981.

As examples of organic UV screening agents, mention may be made of those denoted hereinbelow under their INCI name:

para-Aminobenzoic Acid Derivatives:
PABA,
Ethyl PABA,
Ethyl dihydroxypropyl PABA,
Ethylhexyl dimethyl PABA, sold in particular under the name "Escalol 507" by ISP,
Glyceryl PABA,
PEG-25 PABA, sold under the name "Uvinul P25" by BASF, Salicylic Derivatives:
Homosalate, sold under the name "Eusolex HMS" by Rona/EM Industries,
Ethylhexyl salicylate, sold under the name "Neo Heliopan OS" by Symrise,
Dipropylene glycol salicylate, sold under the name "Dipsal" by Scher,
TEA salicylate, sold under the name "Neo Heliopan TS" by Symrise, Cinnamic Derivatives:
Ethylhexyl methoxycinnamate, sold in particular under the trade name "Parsol MCX" by DSM Nutritional Products,
Isopropyl methoxycinnamate,
Isoamyl methoxycinnamate, sold under the trade name "Neo Heliopan E 1000" by Symrise,
Cinoxate,
DEA methoxycinnamate,
Diisopropyl methylcinnamate,
Glyceryl ethylhexanoate dimethoxycinnamate β,β-Diphenylacrylate derivatives:
Octocrylene, sold especially under the trade name "Uvinul N539" by BASF,
Etocrylene, sold especially under the trade name "Uvinul N35" by BASF, Benzylidene Camphor Derivatives:
3-Benzylidene camphor, manufactured under the name "Mexoryl SD" by Chimex,
4-Methylbenzylidene camphor, sold under the name "Eusolex 6300" by Merck, Polyacrylamidomethyl benzylidene camphor, manufactured under the name "Mexoryl SW" by Chimex, Phenylbenzimidazole Derivatives:
Phenylbenzimidazole sulphonic acid, sold in particular under the trade name "Eusolex 232" by Merck, Phenylbenzotriazole Derivatives:
Methylene bis-benzotriazolyl tetramethylbutylphenol, sold in solid form under the trade name "Mixxim BB/100" by Fairmount Chemical, or in micronized form as an aqueous dispersion under the trade name "Tinosorb M" by Ciba Specialty Chemicals.

Triazine Derivatives:
Bis-ethylhexyloxyphenol methoxyphenyl triazine, sold under the trade name "Tinosorb S" by Ciba Geigy,
Ethylhexyl triazone, sold in particular under the trade name "Uvinul T150" by BASF,
Diethylhexyl butamido triazone, sold under the trade name "Uvasorb HEB" by Sigma 3V,
2,4,6-Tris(diisobutyl 4'-aminobenzalmalonate)-s-triazine,
2,4,6-Tris(dineopentyl 4'-aminobenzalmalonate)-s-triazine,
2,4-Bis(dineopentyl 4'-aminobenzalmalonate)-6-(n-butyl 4'-aminobenzoate)-s-triazine,
the symmetrical triazine screening agents described in U.S. Pat. No. 6,225,467, Patent Application WO 2004/085412 (see compounds 6 and 9) or the document "Symmetrical Triazine Derivatives", IP.COM Journal, IP.COM INC, West Henrietta, N.Y., US (20 Sep. 2004), especially 2,4,6-tris(biphenyl)-1,3,5-triazines (in particular 2,4,6-tris(biphenyl-4-yl)-1,3,5-triazine) and 2,4,6-tris(terphenyl)-1,3,5-triazine, which is also mentioned in Beiersdorf Patent Applications WO 06/035000, WO 06/034982, WO 06/034991, WO 06/035007, WO 2006/034992 and WO 2006/034985.

Anthranilic Derivatives:
Menthyl anthranilate, sold under the trade name "Neo Heliopan MA" by Symrise, Imidazoline Derivatives:
Ethylhexyl dimethoxybenzylidene dioxoimidazoline propionate, Benzalmalonate Derivatives:
Dineopentyl 4'-methoxybenzalmalonate,
Polyorganosiloxane containing benzalmalonate functional groups, for instance Polysilicone-15, sold under the trade name "Parsol SLX" by DSM Nutritional Products.

4,4-Diarylbutadiene Derivatives:
1,1-Dicarboxy(2,2'-dimethylpropyl)-4,4-diphenylbutadiene, Benzoxazole Derivatives:
2,4-Bis[4-[5-(1,1-dimethylpropyl)benzoxazol-2-yl]phenylimino]-6-(2-ethyl hexyl)-imino-1,3,5-triazine, sold under the name "Uvasorb K2A" by Sigma 3V, and mixtures thereof.

The preferential additional organic screening agents are chosen from:
Ethylhexyl methoxycinnamate,
Homosalate,
Ethylhexyl salicylate,
Octocrylene,
Phenylbenzimidazole sulphonic acid,
4-Methylbenzylidene camphor,
Ethylhexyl triazone,
Bis-ethylhexyloxyphenol methoxyphenyl triazine,
Diethylhexyl butamido triazone,
2,4,6-Tris(biphenyl-4-yl)-1,3,5-triazine,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
Methylene bis-benzotriazolyl tetramethylbutylphenol,
Polysilicone-15,
Dineopentyl 4'-methoxybenzalmalonate,
1,1-Dicarboxy(2,2'-dimethylpropyl)-4,4-diphenylbutadiene,
2,4-Bis[4-[5-(1,1-dimethylpropyl)benzoxazol-2-yl]phenylimino]-6-(2-ethylhexyl)-imino-1,3,5-triazine,
and mixtures thereof.

The additional inorganic screening agents are chosen from coated or uncoated metal oxide pigments, the mean size of the primary particles of which is preferably between 5 nm and 100 nm (preferably between 10 nm and 50 nm), such as, for example, pigments formed of titanium oxide (amorphous or crystalline in the rutile and/or anatase form), iron oxide, zinc oxide, zirconium oxide or cerium oxide, which are all UV photoprotective agents well known per se.

The pigments can be coated or uncoated.

The coated pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal alkoxides (titanium or aluminium alkoxides), polyethylene, silicones, proteins (collagen, elastin), alkanolamines, silicon oxides, metal oxides or sodium hexametaphosphate.

As is known, silicones are organosilicon polymers or oligomers of linear or cyclic, branched or crosslinked structure, of variable molecular weight, obtained by polymerization and/or polycondensation of suitably functionalized silanes, and consist essentially of a repetition of main units in which the silicon atoms are linked together via oxygen atoms (siloxane bond), optionally substituted hydrocarbon radicals being directly attached via a carbon atom to the said silicon atoms.

The term "silicones" also includes the silanes required for their preparation, in particular alkylsilanes.

The silicones used for the coating of the pigments suitable for the present invention are preferably chosen from the group consisting of alkylsilanes, polydialkylsiloxanes and polyalkylhydrosiloxanes. More preferably still, the silicones are chosen from the group containing octyltrimethylsilane, polydimethylsiloxanes and polymethylhydrosiloxanes.

Of course, before being treated with silicones, the metal oxide pigments may have been treated with other surface agents, in particular with cerium oxide, alumina, silica, aluminium compounds or silicon compounds, or mixtures thereof.

The coated pigments are more particularly titanium oxides that have been coated:

with silica, such as the product Sunveil from the company Ikeda and the product Eusolex T-AVO from the company Merck, with silica and iron oxide, such as the product Sunveil F from the company Ikeda, with silica and alumina, such as the products Microtitanium Dioxide MT 500 SA and Microtitanium Dioxide MT 100 SA from the company Tayca, Tioveil from the company Tioxide and Mirasun TiW 60 from the company Rhodia, with alumina, such as the products Tipaque TTO-55 (B) and Tipaque TTO-55 (A) from the company Ishihara and UVT 14/4 from the company Kemira, with alumina and aluminium stearate, such as the product Microtitanium Dioxide MT 100 TV, MT 100 TX, MT 100 Z and MT-01 from the company Tayca, and the products Solaveil CT-10 W, Solaveil CT 100 and Solaveil CT 200 from the company Uniqema, with silica, alumina and alginic acid, such as the product MT-100 AQ from the company Tayca, with alumina and aluminium laurate, such as the product Microtitanium Dioxide MT 100 S from the company Tayca, with iron oxide and iron stearate, such as the product Microtitanium Dioxide MT 100 F from the company Tayca, with zinc oxide and zinc stearate, such as the product BR351 from the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminium stearate and treated with a silicone, such as the product STT-30-DS from the company Titan Kogyo, with silica and treated with a silicone, such as the product UV-Titan X 195 from the company Kemira, or the product SMT-100 WRS from the company Tayca, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca.

Other titanium oxide pigments treated with a silicone are preferably $TiO_2$ treated with octyltrimethylsilane and for which the mean size of the elementary particles is between 25 and 40 nm, such as the product sold under the trade name T 805 by the company Degussa Silices, $TiO_2$ treated with a polydimethylsiloxane and for which the mean size of the elementary particles is 21 nm, such as the product sold under the trade name 70250 Cardre UF TiO2SI3 by the company Cardre, anatase/rutile $TiO_2$ treated with a polydimethylhydrosiloxane and for which the mean size of the elementary particles is 25 nm, such as the product sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wacker under the name Transparent titanium oxide PW, by the company Miyoshi Kasei under the name UFTR, by the company Tomen under the name ITS and by the company Tioxide under the name Tioveil AQ.

The uncoated zinc oxide pigments are, for example:

those sold under the name Z-Cote by the company Sunsmart;

those sold under the name Nanox by the company Elementis;

those sold under the name Nanogard WCD 2025 by the company Nanophase Technologies.

The coated zinc oxide pigments are, for example:

those sold under the name Z-Cote HP1 by the company Sunsmart (dimethicone-coated ZnO);

those sold under the name Zinc Oxide CS-5 by the company Toshibi (ZnO coated with polymethylhydrosiloxane);

those sold under the name Nanogard Zinc Oxide FN by the company Nanophase Technologies (as a 40% dispersion in Finsolv TN, $C_{12}$-$C_{15}$ alkyl benzoate);

those sold under the name Daitopersion ZN-30 and Daitopersion ZN-50 by the company Daito (dispersions in cyclopolymethylsiloxane/oxyethylenated polydimethylsiloxane, containing 30% or 50% of nanozinc oxides coated with silica and polymethylhydrosiloxane);

those sold under the name NFD Ultrafine ZnO by the company Daikin (ZnO coated with perfluoroalkyl phosphate and copolymer based on perfluoroalkylethyl as a dispersion in cyclopentasiloxane);

those sold under the name SPD-Z1 by the company Shin-Etsu (ZnO coated with silicone-grafted acrylic polymer, dispersed in cyclodimethylsiloxane);

those sold under the name Escalol Z100 by the company ISP (alumina-treated ZnO dispersed in the ethylhexyl methoxycinnamate/PVP-hexadecene copolymer/methicone mixture);

those sold under the name Fuji ZnO-SMS-10 by the company Fuji Pigment (ZnO coated with silica and polymethylsilsesquioxane);

those sold under the name Nanox Gel TN by the company Elementis (ZnO dispersed at a concentration of 55% in $C_{12}$-$C_{15}$ alkyl benzoate with hydroxystearic acid polycondensate).

The uncoated cerium oxide pigments are sold, for example, under the name Colloidal Cerium Oxide by the company Rhône-Poulenc.

The uncoated iron oxide pigments are sold, for example, by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220, The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, especially of titanium dioxide and of cerium dioxide, including the equal-weight mixture of silica-coated titanium dioxide and of silica-coated cerium dioxide, sold by the company Ikeda under the name Sunveil A, and also the mixture of titanium dioxide and of zinc dioxide coated with alumina, silica and silicone, such as the product M 261 sold by the company Kemira, or coated with alumina, silica and glycerol, such as the product M 211 sold by the company Kemira.

The additional UV screening agents are generally present in the compositions according to the invention in proportions ranging from 0.01% to 20% by weight relative to the total weight of the composition, and preferably ranging from 0.1% to 10% by weight relative to the total weight of the composition.

The aqueous compositions in accordance with the present invention may also comprise standard cosmetic adjuvants chosen especially from fatty substances, organic solvents, ionic or nonionic, hydrophilic or lipophilic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, acidifying or basifying agents or any other ingredient usually used in cosmetics and/or dermatology.

The fatty substances may consist of an oil or a wax other than the apolar waxes as defined above, or mixtures thereof. The term oil means a compound that is liquid at room temperature. The term wax means a compound that is solid or substantially solid at room temperature and whose melting point is generally greater than 35° C.

Mention may be made, as oils, of mineral (paraffin) oils; vegetable oils (sweet almond, macadamia, blackcurrant seed or jojoba oil); synthetic oils, such as perhydrosqualene, alcohols, fatty amides (such as isopropyl lauroyl sarcosinate, sold under the name "Eldew SL-205" by Ajinomoto), fatty acids or esters, such as $C_{12}$-$C_{15}$ alkyl benzoate, sold under the trade name "Finsolv TN" or "Witconol TN" by Witco, 2-ethylphenyl benzoate, such as the product sold under the name X-TEND 226® by ISP, octyl palmitate, isopropyl lanolate, triglycerides, including those of capric/caprylic acids, dicaprylyl carbonate (sold under the name "Cetiol CC" by Cognis), oxyethylenated or oxypropylenated fatty esters and ethers; silicone oils (cyclomethicone, polydimethylsiloxanes or PDMSs) or fluorinated oils, polyalkylenes or trialkyl trimellitates, such as tridecyl trimellitate.

Waxy compounds that may be mentioned include carnauba wax, beeswax, hydrogenated castor oil, polyethylene waxes and polymethylene waxes, for instance the product sold under the name Cirebelle 303 by the company Sasol.

Among the organic solvents that may be mentioned are lower alcohols and polyols. These can be chosen from glycols and glycol ethers, such as ethylene glycol, propylene glycol, butylene glycol, caprylyl glycol, pentylene glycol, dipropylene glycol or diethylene glycol.

Hydrophilic thickeners that may be mentioned include carboxyvinyl polymers, such as Carbopols (Carbomers) and the Pemulens (acrylate/$C_{10}$-$C_{30}$ alkyl acrylate copolymer); polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by Seppic; optionally crosslinked and/or neutralized polymers and copolymers of 2-acrylamido-2-methylpropanesulphonic acid, such as the poly(2-acrylamido-2-methylpropanesulphonic acid) sold by Clariant under the trade name "Hostacerin AMPS" (CTFA name: ammonium polyacryloyldimethyltaurate) or Simulgel 800, sold by Seppic (CTFA name: sodium polyacryloyldimethyl taurate/polysorbate 80/sorbitan oleate); copolymers of 2-acrylamido-2-methylpropanesulphonic acid and of hydroxyethyl acrylate, such as Simulgel NS and Sepinov EMT 10, sold by Seppic; cellulose derivatives, such as hydroxyethylcellulose; polysaccharides and in particular gums, such as xanthan gum; water-soluble or water-dispersible silicone derivatives, such as acrylic silicones, silicone polyethers and cationic silicones; and their mixtures.

Mention may be made, as lipophilic thickeners, of synthetic polymers, such as the poly($C_{10}$-$C_{30}$ alkyl acrylates) sold under the names "Intelimer IPA 13-1" and "Intelimer IPA 13-6" by Landec, or of modified clays, such as hectorite and its derivatives, for example the products sold under the Bentone names.

Of course, a person skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s), especially the improvement in the photostability of the dibenzoylmethane derivative.

The compositions according to the invention may be prepared according to the techniques that are well known to those skilled in the art. They may in particular be in the form of a simple or complex emulsion (O/W, W/O, O/W/O or W/O/W), such as a cream, a milk or a cream-gel; in the form of an aqueous gel; in the form of a lotion. They may optionally be packaged as an aerosol and may be in the form of a mousse or a spray.

The compositions according to the invention are preferably in the form of an oil-in-water or water-in-oil emulsion.

The emulsification processes that may be used are of the paddle or propeller, rotor-stator or HHP type.

It is also possible, via HHP (between 50 and 800 bar), to obtain stable dispersions with drop sizes that may be as low as 100 nm.

The emulsions generally contain at least one emulsifier chosen from amphoteric, anionic, cationic or nonionic emulsifiers, used alone or as a mixture. The emulsifiers are appropriately chosen according to the emulsion to be obtained (W/O or O/W).

As emulsifying surfactants that may be used for the preparation of the W/O emulsions, examples that may be mentioned include alkyl esters or ethers of sorbitan, of glycerol or of sugars; silicone surfactants, for instance dimethicone copolyols, such as the mixture of cyclomethicone and of dimethicone copolyol, sold under the name DC 5225 C by the company Dow Corning, and alkyl dimethicone copolyols such as lauryl methicone copolyol, sold under the name Dow Corning 5200 Formulation Aid by the company Dow Corning; cetyl dimethicone copolyol, such as the product sold under the name Abil EM 90R by the company Goldschmidt, and the mixture of cetyl dimethicone copolyol, of polyglyceryl isostearate (4 mol) and of hexyl laurate sold under the name Abil WE O9 by the company Goldschmidt. One or more co-emulsifiers may also be added thereto, which may be chosen advantageously from the group comprising polyol alkyl esters.

Polyol alkyl esters that may especially be mentioned include polyethylene glycol esters, for instance PEG-30 dipolyhydroxystearate, such as the product sold under the name Arlacel P135 by the company ICI.

Glycerol and/or sorbitan esters that may be mentioned include, for example, polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

For the O/W emulsions, examples of emulsifiers that may be mentioned include nonionic emulsifiers such as oxyalkylenated (more particularly polyoxyethylenated) esters of fatty acids and of glycerol; oxyalkylenated esters of fatty acids and of sorbitan; oxyalkylenated (oxyethylenated and/or oxypropylenated) esters of fatty acids, such as the PEG 100 stearate/glyceryl stearate mixture sold, for example, by ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by the company Henkel under the respective names Plantaren 2000 and Plantaren 1200, cetostearyl glucoside, optionally as a mixture with cetostearyl alcohol, sold, for example, under the name Montanov 68 by the company Seppic, under the name Tegocare CG90 by the company Goldschmidt and under the name Emulgade KE3302 by the company Henkel, and also arachidyl glucoside, for example in the form of the mixture of arachidyl alcohol, behenyl alcohol and arachidyl glucoside sold under the name Montanov 202 by the company Seppic. According to one particular embodiment of the invention, the mixture of the alkyl polyglucoside as defined above with the corresponding fatty alcohol can be in the form of a self-emulsifying composition, for example as described in the document WO-A-92/06778.

When it is an emulsion, the aqueous phase of this emulsion may comprise a nonionic vesicular dispersion prepared according to known processes (Bangham, Standish and Watkins, J. Mol. Biol., 13, 238 (1965), FR 2 315 991 and FR 2 416 008).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

Another subject-matter of the present invention consists of the use of the compositions according to the invention as defined above for the manufacture of products for cosmetically treating the skin, the lips, the nails, the hair, the eyelashes, the eyebrows and/or the scalp, especially care products, antisun protection products and makeup products.

The cosmetic compositions according to the invention may be used, for example, as makeup products.

The cosmetic compositions according to the invention may be used, for example, as care products and/or antisun protection products for the face and/or the body, of liquid to semi-liquid consistency, such as milks, more or less rich creams, cream-gels and pastes. They may optionally be packaged as an aerosol and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", aerosol containers comprising a propellant and also aerosol pumps using compressed air as propellant. These devices are described in U.S. Pat. No. 4,077,441 and U.S. Pat. No. 4,850,517 (which form an integral part of the content of the description).

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The compositions according to the invention may also comprise additional cosmetic or dermatological active agents.

Mention may be made, among active agents, of:
vitamins (A, C, E, K, PP, and the like) and their derivatives or precursors, alone or as mixtures;
antiglycation agents;
calmatives;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
tensioning agents;
matting agents;
keratolytic agents;
desquamating agents;
moisturizers, for instance polyols, such as glycerol, butylene glycol or propylene glycol;
antiinflammatory agents;
agents that act on the energy metabolism of cells;
insect repellents;
substance P or CRGP antagonists;
hair-loss counteractants and/or hair restorers;
anti-wrinkle agents.

Of course, a person skilled in the art will take care to select the aforementioned optional additional compound(s) and/or the amounts thereof such that the advantageous properties intrinsically associated with the compositions in accordance with the invention are not, or are not substantially, adversely affected by the envisaged addition(s).

A person skilled in the art will select the said active agent(s) as a function of the effect desired on the skin, the hair, the eyelashes, the eyebrows and the nails.

The composition may also comprise at least one ingredient, such as fillers with a soft-focus effect or agents for promoting the natural coloration of the skin, intended for complementing the biological effect of these active agents or for providing an immediate visual anti-ageing effect.

For caring for and/or making up greasy skin, a person skilled in the art will preferably select at least one active agent chosen from desquamating agents, sebum-regulating or anti-seborrhoeic agents, and astringents.

Other Additional Ingredients

The composition may also comprise at least one additional ingredient for complementing the biological effect of these active agents or for providing an immediate visual effect; mention may be made especially of matting agents, fillers with a soft-focus effect, fluorescers, agents for promoting the naturally pinkish coloration of the skin, and abrasive fillers or exfoliants.

To complement and/or optimize the effects imparted by the cosmetic and/or dermatological active agents mentioned above on the keratin materials, it may be advantageous to incorporate into the compositions of the invention other additional ingredients.

In particular, these additional ingredients may impart an immediate visual effect that will be relayed by the biological effect of the active agents mentioned above. They may also, via a mechanical action (e.g.: abrasive fillers), amplify the effect of the biological active agents mentioned above.

Thus, the composition according to the invention can additionally comprise at least one agent chosen from matting agents, fillers with a soft-focus effect, agents for promoting the naturally pinkish coloration of the skin, abrasive fillers or exfoliants, and mixtures thereof.

Matting Agents

The term "matting agent" means agents intended to make the skin visibly more matt and less shiny.

The matting effect of the agent and/or composition containing it may especially be evaluated using a gonioreflectometer, by measuring the ratio R between the specular reflection and the scattered reflection. A value of R of less than or equal to 2 generally indicates a matting effect.

The matting agent may especially be chosen from a rice starch or a maize starch: INCI name: *Zea mays* (Corn) Starch, such as, in particular, the product sold under the trade name Farmal CS 3650 Plus 036500 by National Starch, kaolinite, talc, a pumpkin seed extract, cellulose microbeads, plant fibres, synthetic fibres, in particular polyamide fibres, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof.

Examples of matting agents that may especially be mentioned include:
  rice or maize starch, in particular an aluminium starch octenyl succinate sold under the name Dry Flo® by the company National Starch;
  kaolinite;
  silicas;
  talc;
  a pumpkin seed extract as sold under the name Curbilene® by the company Indena;
  cellulose microbeads as described in Patent Application EP 1 562 562;
  fibres, such as silk fibres, cotton fibres, wool fibres, flax fibres, cellulose fibres extracted especially from wood, from vegetables or from algae, polyamide (Nylon®) fibres, modified cellulose fibres, poly-p-phenylene terephthalamide fibres, acrylic fibres, polyolefin fibres, glass fibres, silica fibres, aramid fibres, carbon fibres, Teflon® fibres, insoluble collagen fibres, polyester fibres, polyvinyl chloride or polyvinylidene chloride fibres, polyvinyl alcohol fibres, polyacrylonitrile fibres, chitosan fibres, polyurethane fibres, polyethylene phthalate fibres, fibres formed from a mixture of polymers, resorbable synthetic fibres, and mixtures thereof described in Patent Application EP 1 151 742;
  expanded acrylic copolymer microspheres, such as those sold by the company Expancel under the name Expancel 551®;
  fillers with an optical effect as described in Patent Application FR 2 869 796, in particular:
  polyamide (Nylon®) powders, for instance Nylon 12 particles of the Orgasol type from Arkema, with a mean size of 10 microns and a refractive index of 1.54,
  silica powders, for instance Silica beads SB150 from Miyoshi with a mean size of 5 microns and a refractive index of 1.45,
  polytetrafluoroethylene powders, for instance PTFE Ceridust 9205F from Clariant, with a mean size of 8 microns and a refractive index of 1.36,
  silicone resin powders, for instance the silicone resin Tospearl 145A from GE Silicone with a mean size of 4.5 microns and a refractive index of 1.41,
  acrylic copolymer powders, especially of polymethyl (meth)acrylate, for instance the PMMA particles Jurymer MBI from Nihon Junyoki, with a mean size of 8 microns and a refractive index of 1.49, or the Micropearl M100® and F 80 ED® particles from the company Matsumoto Yushi-Seiyaku,
  wax powders, for instance the paraffin wax particles Microease 114S from Micropowders, with a mean size of 7 microns and a refractive index of 1.54,
  polyethylene powders, especially comprising at least one ethylene/acrylic acid copolymer, and in particular consisting of ethylene/acrylic acid copolymers, for instance the particles Flobeads EA 209 from Sumitomo (with a mean size of 10 microns and a refractive index of 1.48),
  elastomeric crosslinked organopolysiloxane powders coated with silicone resin, especially with silsesquioxane resin, as described, for example, in U.S. Pat. No. 5,538,793. Such elastomer powders, are sold under the names KSP-100, KSP-101, KSP-102, KSP-103, KSP-104 and KSP-105 by the company Shin-Etsu, and
  talc/titanium dioxide/alumina/silica composite powders, such as those sold under the name Coverleaf® AR-80 by the company Catalyst & Chemicals,
  mixtures thereof,
  compounds that absorb and/or adsorb sebum as described in Patent Application FR 2 869 796. Mention may be made especially of:
  silica powders, for instance the porous silica microspheres sold under the name Silica Beads SB-700 by the company Miyoshi, the products Sunsphere® H51, Sunsphere® H33 and Sunsphere® H53 sold by the company Asahi Glass; the polydimethylsiloxane-coated amorphous silica microspheres sold under the names SA Sunsphere® H-33 and SA Sunsphere® H-53 by the company Asahi Glass;
  powders of amorphous mixed silicates, especially of aluminium and magnesium, for instance the product sold under the name Neusilin UFL2 by the company Sumitomo;
  polyamide (Nylon®) powders, for instance Orgasol® 4000 sold by the company Arkema, and
  acrylic polymer powders, especially of polymethyl methacrylate, for instance Covabead® LH85 sold by the company Wacker; of polymethyl methacrylate/ethylene glycol dimethacrylate, for instance Dow Corning 5640 Microsponge® Skin Oil Adsorber sold by the company Dow Corning, or Ganzpearl® GMP-0820 sold by the company Ganz Chemical; of polyallyl methacrylate/ethylene glycol dimethacrylate, for instance Poly-Pore® L200 or Poly-Pore® E200 sold by the company Amcol; of ethylene glycol dimethacrylate/lauryl methacrylate copolymer, for instance Polytrap® 6603 sold by the company Dow Corning;
  silicate particles, such as alumina silicate;
  mixed silicate particles, such as:
  magnesium aluminium silicate particles, such as saponite or hydrated magnesium aluminium silicate with a sodium sulphate sold under the trade name Sumecton® by the company Kunimine;
  the magnesium silicate, hydroxyethylcellulose, black cumin oil, marrow oil and phospholipids complex or Matipure® from Lucas Meyer, and
  mixtures thereof.

Preferred matting agents that may be used according to the invention include a pumpkin seed extract, a rice or maize starch, kaolinite, silicas, talc, polyamide powders, polyethylene powders, acrylic copolymer powders, expanded acrylic copolymer microspheres, silicone resin microbeads and mixed silicate particles, and mixtures thereof.

Fillers with a Soft-Focus Effect

These fillers may be any material capable of modifying and hiding wrinkles by virtue of its intrinsic physical properties. These fillers may especially modify wrinkles via a tensioning effect, a covering effect or a soft-focus effect.

The following compounds may be given as examples of fillers:

porous silica microparticles, for instance Silica Beads® SB150 and SB700 from Miyoshi with a mean size of 5 μm and the Sunsphere® series H products from Asahi Glass, for instance the H33 and H51 products with respective sizes of 3.5 and 5 μm;

hollow hemispherical silicone resin particles, such as NLK 500®, NLK 506® and NLK 510® from Takemoto Oil and Fat, especially described in EP-A-1 579 849;

silicone resin powders, for instance the silicone resin Tospearl® 145A from GE Silicone, with a mean size of 4.5 μm;

acrylic copolymer powders, especially of polymethyl (meth)acrylate, for instance the PMMA particles Jurymer MBI® from Nihon Junyoki, with a mean size of 8 μm, the hollow PMMA spheres sold under the name Covabead® LH85 by the company Wacker, and the vinylidene/acrylonitrile/methyl methacrylate expanded microspheres sold under the name Expancel®;

wax powders, for instance the paraffin wax particles MicroEase® 114S from MicroPowders, with a mean size of 7 μm;

polyethylene powders, especially comprising at least one ethylene/acrylic acid copolymer, for instance the Flobeads® EA 209 E product from Sumitomo, with a mean size of 10 μm;

crosslinked elastomeric organopolysiloxane powders coated with silicone resin and especially with silsesquioxane resin, sold under the names KSP-100®, KSP-101®, KSP-102®, KSP-103®, KSP-104® and KSP-105® by the company Shin-Etsu;

talc/titanium dioxide/alumina/silica composite powders, for instance the Coverleaf AR-80® products from the company Catalyst & Chemicals;

talc, mica, kaolin, lauryl glycine, starch powders crosslinked with octenyl-succinic anhydride, boron nitride, polytetrafluoroethylene powders, precipitated calcium carbonate, magnesium carbonate, basic magnesium carbonate, barium sulphate, hydroxyapatite, calcium silicate, cerium dioxide and glass or ceramic microcapsules;

hydrophilic or hydrophobic, synthetic or natural, mineral or organic fibres, such as silk fibres, cotton fibres, wool fibres, flax fibres, cellulose fibres extracted especially from wood, vegetables or algae, polyamide (Nylon®) fibres, modified cellulose fibres, poly-p-phenylene terephthalamide fibres, acrylic fibres, polyolefin fibres, glass fibres, silica fibres, aramid fibres, carbon fibres, polytetrafluoroethylene (Teflon®) fibres, insoluble collagen fibres, polyester fibres, polyvinyl chloride fibres, polyvinylidene chloride fibres, polyvinyl alcohol fibres, polyacrylonitrile fibres, chitosan fibres, polyurethane fibres, polyethylene phthalate fibres, fibres formed from a mixture of polymers, resorbable synthetic fibres, and mixtures thereof described in Patent Application EP 1 151 742;

spherical elastomeric crosslinked silicones, for instance Trefil E-505C® or E-506C® from Dow Corning;

abrasive fillers, which, via a mechanical effect, smooth out the skin microrelief, such as abrasive silica, for instance Abrasif SP® from Semanez or nut or shell powders (for example of apricot or walnut, from Cosmetochem).

The fillers having an effect on the signs of ageing are chosen in particular from porous silica microparticles, hollow hemispherical silicone particles, silicone resin powders, acrylic copolymer powders, polyethylene powders, crosslinked elastomeric organopolysiloxane powders coated with silicone resin, talc/titanium dioxide/alumina/silica composite powders, precipitated calcium carbonate, magnesium carbonate, basic magnesium carbonate, barium sulphate, hydroxyapatite, calcium silicate, cerium dioxide, glass or ceramic microcapsules, silk or cotton fibres, and mixtures thereof.

The filler may be a filler with a soft-focus effect.

The term "filler with a soft-focus effect" means a filler which in addition gives the complexion transparency and a hazy effect. Preferably, the fillers with a soft-focus effect have a mean particle size of less than or equal to 15 microns. These particles may be in any form and in particular may be spherical or non-spherical. These fillers are more preferably non-spherical.

The fillers with a soft-focus effect can be chosen from silica and silicate powders, in particular alumina powders, powders of polymethyl methacrylate (PMMA) type, talc, silica/$TiO_2$ or silica/zinc oxide composites, polyethylene powders, starch powders, polyamide powders, styrene/acrylic copolymer powders, silicone elastomers and mixtures thereof.

Mention may be made in particular of talc with a number-average size of less than or equal to 3 microns, for example talc with a number-average size of 1.8 microns and especially the product sold under the trade name Talc P3® by the company Nippon Talc, Nylon® 12 powder, especially the product sold under the name Orgasol 2002 Extra D Nat Cos® by the company Atochem, silica particles 1% to 2% surface-treated with a mineral wax (INCI name: hydrated silica (and) paraffin), such as the products sold by the company Degussa, amorphous silica microspheres, such as the products sold under the name Sunsphere, for example of reference H-53® by the company Asahi Glass, and silica microbeads, such as those sold under the name SB-700® or SB-150® by the company Miyoshi, this list not being limiting.

The concentration of these fillers with an effect on the signs of ageing in the compositions according to the invention may be between 0.1% and 40% or even between 0.1% and 20% by weight, relative to the total weight of the composition.

Agents for Promoting the Naturally Pinkish Coloration of the Skin

Mention may be made especially of:

a self-tanning agent, i.e. an agent which, when applied to the skin, especially to the face, can produce a tanning effect that is more or less similar in appearance to that which may result from prolonged exposure to the sun (natural tanning) or under a UV lamp;

an additional colouring agent, i.e. any compound that has a particular affinity for the skin, which allows it to give the skin a lasting and non-covering (i.e. that does not have a tendency to opacify the skin) coloration and that is not removed either with water or using a solvent, and that withstands both rubbing and washing with a solution containing surfactants. Such a lasting coloration is thus distinguished from the superficial and transient coloration provided, for example, by a makeup pigment;

and mixtures thereof.

Examples of self-tanning agents that may especially be mentioned include:
dihydroxyacetone (DHA),
erythrulose, and
the combination of a catalytic system formed from:
manganese and/or zinc salts and oxides, and
alkali metal and/or alkaline earth metal hydrogen carbonates.

The self-tanning agents are generally chosen from monocarbonyl or polycarbonyl compounds, for instance isatin, alloxan, ninhydrin, glyceraldehyde, mesotartaric aldehyde, glutaraldehyde, erythrulose, pyrazoline-4,5-dione derivatives as described in Patent Applications FR 2 466 492 and WO 97/35842, dihydroxyacetone (DHA) and 4,4-dihydroxypyrazolin-5-one derivatives as described in Patent Application EP 903 342. DHA will preferably be used.

DHA may be used in free and/or encapsulated form, for example encapsulated in lipid vesicles, such as liposomes, especially described in Patent Application WO 97/25970.

In general, the self-tanning agent is present in an amount ranging from 0.01% to 20% by weight and preferably in an amount of between 0.1% and 10% of the total weight of the composition.

Other dyes that allow modification of the colour produced by the self-tanning agent may also be used.

These dyes may be chosen from synthetic or natural direct dyes.

These dyes may be chosen, for example, from red or orange dyes of the fluoran type, such as those described in Patent Application FR 2 840 806. Mention may be made, for example, of the following dyes:
tetrabromofluorescein or eosin, known under the CTFA name: CI 45380 or Red 21
phloxin B, known under the CTFA name: CI 45410 or Red 27
diiodofluorescein, known under the CTFA name: CI 45425 or Orange 10;
dibromofluorescein, known under the CTFA name: CI 45370 or Orange 5;
the sodium salt of tetrabromofluorescein, known under the CTFA name: CI 45380 (Na salt) or Red 22;
the sodium salt of phloxin B, known under the CTFA name: CI 45410 (Na salt) or Red 28;
the sodium salt of diiodofluorescein, known under the CTFA name: CI 45425 (Na salt) or Orange 11;
erythrosine, known under the CTFA name: CI 45430 or Acid Red 51.
phloxin, known under the CTFA name: CI 45405 or Acid Red 98.

These dyes may also be chosen from anthraquinones, caramel, carmine, carbon black, azulene blues, methoxalen, trioxalen, guaiazulene, chamazulene, rose Bengal, eosin 10B, cyanosin and daphinin.

These dyes may also be chosen from indole derivatives, for instance the monohydroxyindoles as described in Patent FR 2 651 126 (i.e.: 4-, 5-, 6- or 7-hydroxyindole) or the dihydroxyindoles as described in Patent EP-B-0 425 324 (i.e.: 5,6-dihydroxyindole, 2-methyl-5,6-dihydroxyindole, 3-methyl-5,6-dihydroxyindole or 2,3-dimethyl-5,6-dihydroxyindole).

Abrasive Fillers or Exfoliants

As exfoliants that may be used in rinse-out compositions according to the invention, examples that may be mentioned include exfoliant or scrubbing particles of mineral, plant or organic origin. Thus, polyethylene beads or powder, Nylon powder, polyvinyl chloride powder, pumice powder, ground apricot kernel or walnut husk, sawdust, glass beads and alumina, and mixtures thereof, may be used, for example. Mention may also be made of Exfogreen® from Solabia (bamboo extract), extracts of strawberry achenes (Strawberry achenes from Greentech), peach kernel powder, apricot kernel powder, and finally, in the field of plant powders with an abrasive effect, mention may be made of cranberry seed powder.

As abrasive fillers or exfoliants that are preferred according to the invention, mention will be made of peach kernel powder, apricot kernel powder, cranberry seed powder, strawberry achene extracts and bamboo extracts.

The examples that follow serve to illustrate the invention without, however, being limiting in nature. In these examples, the amounts of the composition ingredients are given as weight percentages relative to the total weight of the composition.

I/Examples of the Synthesis of the Triazines of Formula (III):

Example 1

Preparation of 2,4-bis(methyl 4'-aminobenzoate)-6-{[1,3,3,3-tetramethyl-1-[(trimethylsilyl)oxy]disiloxanyl]propyl-3-ylamino}-s-triazine (Route 1)

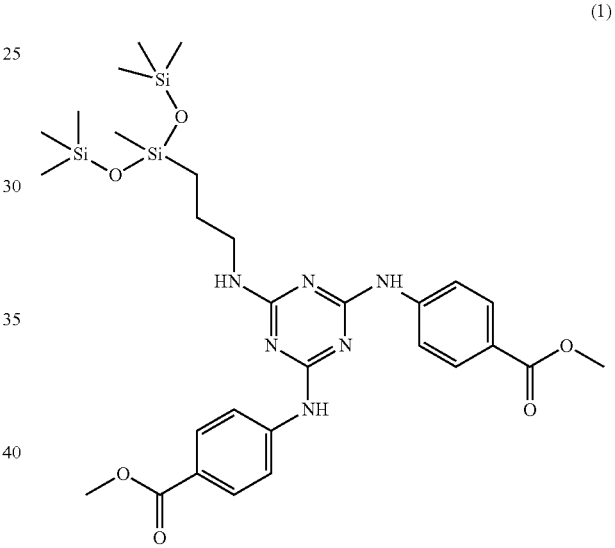

(1)

Methyl para-aminobenzoate (9.2 g, 0.0609 mol), 2-butanone (40 ml) and potassium carbonate (4.21 g) dissolved in 57 ml of water are successively introduced into a reactor while bubbling with nitrogen. The mixture is cooled to 0-5° C. and cyanuric chloride (5.61 g, 0.0304 mol), dissolved in 88 ml of 2-butanone, is introduced dropwise over 1 hour. The mixture is heated at 70° C. for 6 hours; the 2,4-bis (methyl 4'-aminobenzoate)-6-chloro-s-triazine formed is not isolated.

2.56 g of sodium bicarbonate are added to the reaction mixture and then 1-amino-3-[[1,3,3,3-tetramethyl-1-[(trimethylsilyl)oxy]disiloxanyl]propane (8.51 g, 0.0304 mol) is run in dropwise over 1 hour. After cooling, the 2 phases are separated and the organic phase is washed with water and dried. The 2-butanone is removed under reduced pressure. The paste obtained is purified by passing through a silica column (eluent: heptane/EtOAc 8:2). The clean fractions of the derivative of Example 1 are thus recovered (3.53 g, yield: 18%) in the form of a beige powder:
Melting point: 144-145° C.,
UV (Ethanol): $\lambda_{max}$=311 nm, $E_{1\%}$=1268.

Example 2

Preparation of 2,4-bis(ethyl 4'-aminobenzoate)-6-{[1,3,3,3-tetramethyl-1-[(trimethylsilyl)oxy]disiloxanyl]propyl-3-ylamino}-s-triazine (Route 1)

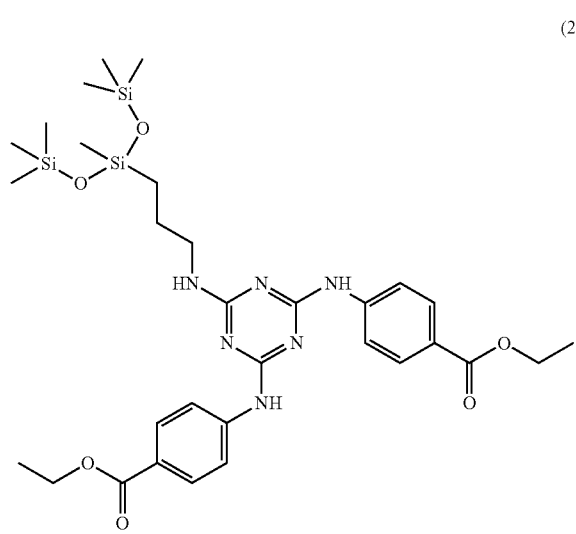 [SMILES: CCOC(=O)c1ccc(Nc2nc(NCCC[Si](C)(O[Si](C)(C)C)O[Si](C)(C)C)nc(Nc3ccc(C(=O)OCC)cc3)n2)cc1]

(2)

Ethyl para-aminobenzoate (6.05 g, 0.0366 mol), 2-butanone (30 ml) and potassium carbonate (2.53 g) dissolved in 38 ml of water are successively introduced into a reactor while bubbling with nitrogen. The mixture is cooled to 0-5° C. and cyanuric chloride (3.38 g, 0.0183 mol), dissolved in 68 ml of 2-butanone, is introduced dropwise over 1 hour. The mixture is heated at 70° C. for 6 hours; the 2,4-bis(ethyl 4'-aminobenzoate)-6-chloro-s-triazine formed is not isolated and is reacted in the following stage.

1.54 g of sodium bicarbonate are added to the reaction mixture and then 1-amino-3-[1,3,3,3-tetramethyl-1-[(trimethylsilyl)oxy]disiloxanyl]propane (5.12 g, 0.0183 mol) is run in dropwise over 1 hour. The mixture is maintained at 70° C. for 4 hours. After cooling, the 2 phases are separated and the organic phase is washed with water and dried. The 2-butanone is removed under reduced pressure. The paste obtained is crystallized from heptane. The product of Example 2 (8.8 g, yield 70%) is thus obtained in the form of light beige crystals:

Melting point: 134-135° C.,

UV (Ethanol): $\lambda_{max}$=311 nm, $E_{1\%}$=1186.

Example 3

Preparation of 2,4-bis(ethyl 4'-aminobenzoate)-6-{[1,3,3,3-tetramethyl-1-[(trimethylsilyl)oxy]disiloxanyl]propyl-3-ylamino}-s-triazine (Route 2)

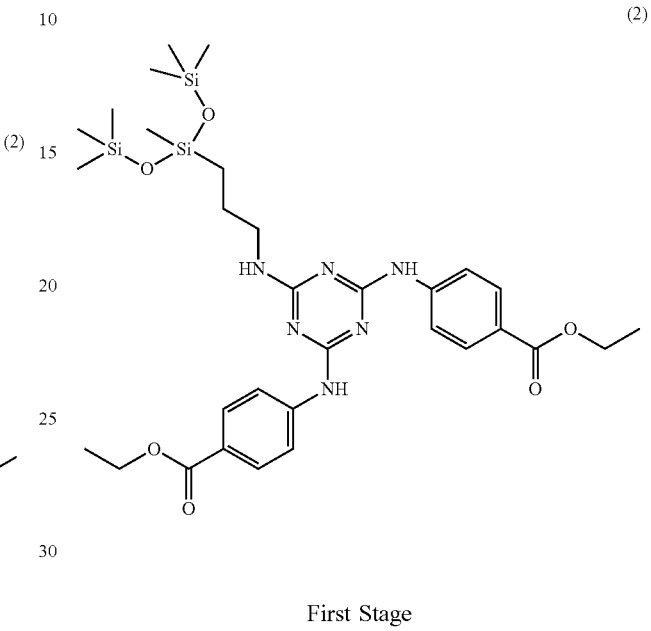

(2)

First Stage

Preparation of 2,4-dichloro-6-{[1,3,3,3-tetramethyl-1-[(trimethylsilyl)-oxy]disiloxanyl]propyl-3-ylamino}-s-triazine 1-Amino-3-[1,3,3,3-tetramethyl-1-[(trimethylsilyl)oxy]disiloxanyl]propane (41.7 g, 0.149 mol) and a solution of sodium bicarbonate (11.4 g, 0.135 mol) in 120 ml of water are added dropwise in 0° C. to a solution of cyanuric chloride (25 g, 0.135 mol) in 250 ml of acetone so that the pH lies between 3 and 6.5. At the end of the introduction, the pH is 6.5. Stirring is subsequently maintained at 10° C. for 1 hour 30 minutes and is then left at laboratory temperature. The precipitate formed is filtered off, washed with water, superficially dewatered and dried. 55.2 g (yield: 95%) of the expected derivative are obtained in the form of a white powder (M.p.: 59° C.).

Second Stage

Preparation of Compound (2)

The mixture of the preceding product (2.1 g, 0.005 mol) and of ethyl para-aminobenzoate (1.65 g, 0.01 mol) in suspension in 20 ml of toluene is heated at reflux for 1 hour 30 minutes. The mixture is cooled and hot heptane is added to the resin obtained. After triturating, filtering and drying, 2.3 g (yield: 67%) of the derivative of Example 3 are obtained in the form of a white powder:

Melting point: 126-128° C.,

UV (Ethanol): $\lambda_{max}$=311 nm, $E_{1\%}$=1147.

Example 4

Preparation of 2,4-bis(n-propyl 4'-aminobenzoate)-6-{[1,3,3,3-tetramethyl-1-[(trimethylsilyl)oxy]disiloxanyl]propyl-3-ylamino}-s-triazine (Route 2)

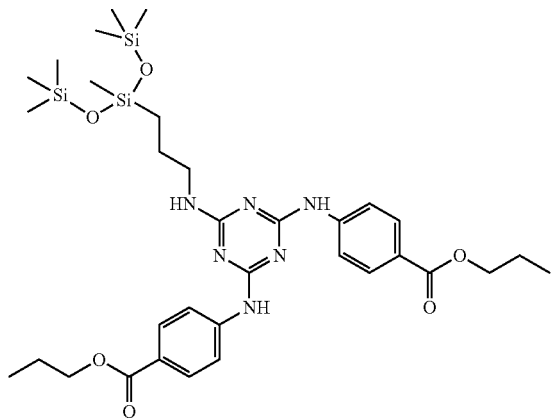

(3)

n-Propyl para-aminobenzoate (3.35 g, 0.0187 mol), dissolved in 15 ml of ethyl acetate, is introduced into a reactor. 1.5 ml of pyridine dissolved in 10 ml of ethyl acetate are added thereto. The reaction mixture is heated to 70° C. under an argon atmosphere and then the product from the first stage of Example 3 (4 g, 0.0094 mol) is added. The mixture is left at 70° C. for 2 hours. The dark red solution is cooled and is washed with saturated sodium chloride solutions and then with water. After drying the organic phase, the paste obtained is crystallized from heptane. The product of Example 4 is thus obtained (2.3 g, yield: 34%) in the form of light beige crystals:

Melting point: 109-110° C.,
UV (Ethanol): $\lambda_{max}$=311 nm, $E_{1\%}$=1228.

Example 5

Preparation of 2,4-bis(isopropyl 4'-aminobenzoate)-6-{[1,3,3,3-tetramethyl-1-[(trimethylsilyl)oxy]disiloxanyl]propyl-3-ylamino}-s-triazine (Route 2)

(4)

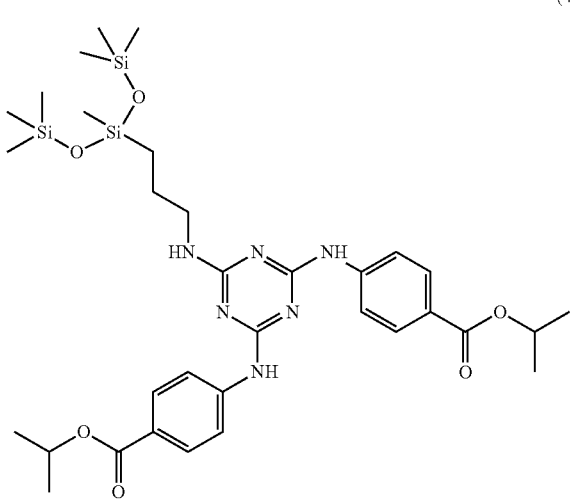

Isopropyl para-aminobenzoate (10.05 g, 0.0561 mol), dissolved in 40 ml of ethyl acetate, is introduced into a reactor. 4.54 ml of pyridine dissolved in 15 ml of ethyl acetate are added thereto. The reaction mixture is heated to 70° C. under an argon atmosphere and then the product from the first stage of Example 3 (12 g, 0.0281 mol) is added. The mixture is left at 70° C. for 2 hours. The dark red solution is cooled and is washed with saturated sodium chloride solutions and then with water. After drying the organic phase, the paste obtained is purified by chromatography on a silica column (eluent: heptane/EtOAc 8:2) and crystallized from heptane. The product of Example 5 is thus obtained (10.8 g, yield: 54%) in the form of a light beige powder:

Melting point: 68-70° C.,
UV (Ethanol): $\lambda_{max}$=311 nm, $E_{1\%}$=1155.

Example 6

Preparation of 2,4-bis(n-butyl 4'-aminobenzoate)-6-{[1,3,3,3-tetramethyl-1-[(trimethylsilyl)oxy]disiloxanyl]propyl-3-ylamino}-s-triazine (Route 2)

(5)

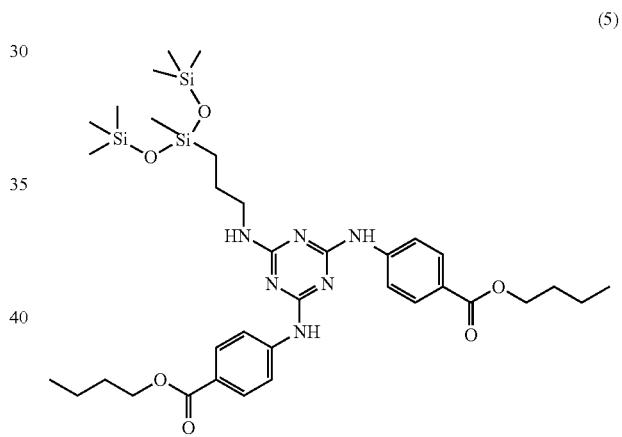

The product obtained in the first stage of Example 3 (16.74 g, 0.0391 mol), n-butyl para-aminobenzoate (15 g, 0.0776 mol) and potassium carbonate (5.36 g, 0.0388 mol) are suspended in 170 ml of toluene and are heated at reflux for 1 hour 20 minutes, while sparging with nitrogen. The reaction mixture is cooled and 150 ml of dichloromethane are added thereto. The inorganic products are filtered off. The filtrate is washed with an aqueous bicarbonate solution and then twice with water. After drying the organic phase and evaporating the solvents, a white powder is obtained. After recrystallizing from an EtOAc/heptane 1:15 mixture, 20.1 g (yield: 69%) of the derivative of Example 6 are obtained in the form of a white powder:

Melting point: 111-113° C.,
UV (Ethanol): $\lambda_{max}$=312 nm, $E_{1\%}$=1360.

Example 7

Preparation of 2,4-bis(isobutyl 4'-aminobenzoate)-6-{[1,3,3,3-tetramethyl-1-[(trimethylsilyl)oxy]disiloxanyl]propyl-3-ylamino}-s-triazine (Route 1)

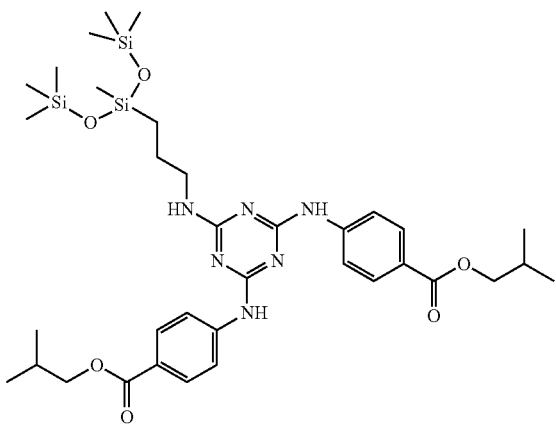

(6)

Isobutyl para-aminobenzoate (10.39 g, 0.0538 mol), 2-butanone (72 ml) and potassium carbonate (3.72 g) dissolved in 57 ml of water are successively introduced into a reactor while bubbling with nitrogen. The mixture is cooled to 0-5° C. and cyanuric chloride (4.96 g, 0.0269 mol), dissolved in 68 ml of 2-butanone, is introduced dropwise over 1 hour 30 minutes. The mixture is heated at 70° C. for 17 hours; the 2,4-bis(isobutyl 4'-aminobenzoate)-6-chloro-s-triazine formed is not isolated.

2.26 g of sodium bicarbonate are added to the reaction mixture and then the product from the first stage of Example 2a (7.52 g, 0.0269 mol) is run in dropwise for 1 hour. After cooling, the 2 phases are separated and the organic phase is washed with water and dried. The 2-butanone is removed under reduced pressure. The paste obtained is chromatographed on a silica column (eluent: heptane/EtOAc 8:2). The product of Example 7 is thus obtained (5.2 g, yield 26%) in the form of light beige crystals:

Melting point: 66-67° C.,
UV (Ethanol): $\lambda_{max}$=311 nm, $E_{1\%}$=1150.

Example 8

Preparation of 2-(methyl 4'-aminobenzoate)-4-(tert-butyl 4''-aminobenzoate)-6-{[1,3,3,3-tetramethyl-1-[(trimethylsilyl)oxy]disiloxanyl]propyl-3-ylamino}-s-triazine (Route 1, modified)

(7)

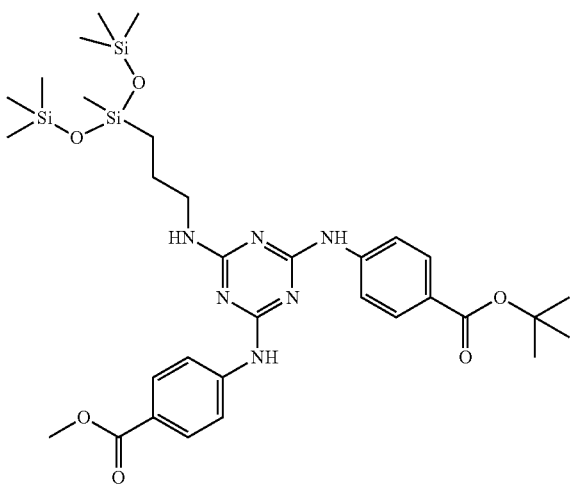

tert-Butyl para-aminobenzoate (1 g, 0.00517 mol) is dissolved in 10 ml of ethyl acetate in a reactor while bubbling with nitrogen. Pyridine (836 µl), dissolved in 5 ml of ethyl acetate, is added thereto. The mixture is heated to 70° C. and a solution of the derivative from the first stage of Example 2a (2.21 g, 0.00517 mol) in 15 ml of ethyl acetate is run in dropwise over 30 minutes. The mixture is left at 70° C. for 2 hours and a solution of para-aminobenzoate (0.98 g, 0.00517 mol) dissolved in 5 ml of ethyl acetate is subsequently added. Heating is continued at 70° C. for 2 hours. After cooling, the organic phase is washed with a saturated sodium chloride solution and then with water and dried. The paste obtained is chromatographed on a silica column (eluent: heptane/EtOAc 8:2). The product of Example 8 is thus obtained (1.52 g, yield 30%) in the form of light beige crystals:

Melting point: 111-113° C.,
UV (Ethanol): $\lambda_{max}$=311 nm, $E_{1\%}$=1425.

Example 9

Preparation of 2,4-bis(tert-butyl 4'-aminobenzoate)-6-{[1,3,3,3-tetramethyl-1-[(trimethylsilyl)oxy]disiloxanyl]propyl-3-ylamino}-s-triazine (Route 2)

(8)

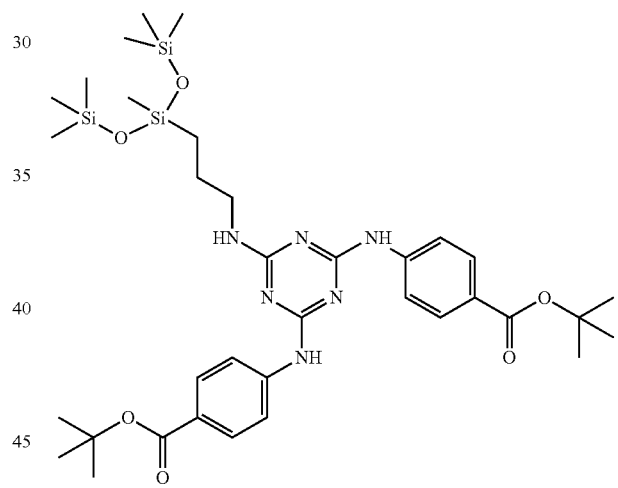

tert-Butyl para-aminobenzoate (3.62 g, 0.0189 mol) is dissolved in 15 ml of ethyl acetate in a reactor while bubbling with nitrogen. Pyridine (1.5 ml), dissolved in 10 ml of ethyl acetate, is added thereto. The mixture is heated to 70° C. and a solution of the derivative from the first stage of Example 3 (4 g, 0.00936 mol) in 15 ml of ethyl acetate is run in dropwise over 30 minutes. The mixture is left at 70° C. for 2 hours. After cooling, the organic phase is washed with a saturated sodium chloride solution and then with water and dried. The paste obtained is chromatographed on a silica column (eluent: heptane/EtOAc 8:2). The clean fractions of the product of Example 9 are thus obtained (3.94 g, yield 42%) in the form of a white powder:

Melting point: 78-79° C.,
UV (Ethanol): $\lambda_{max}$=311 nm, $E_{1\%}$=1321.

Example 10

Preparation of 2,4-bis(n-pentyl 4'-aminobenzoate)-6-{[1,3,3,3-tetramethyl-1-[(trimethylsilyl)oxy]disiloxanyl]propyl-3-ylamino}-s-triazine (Route 1)

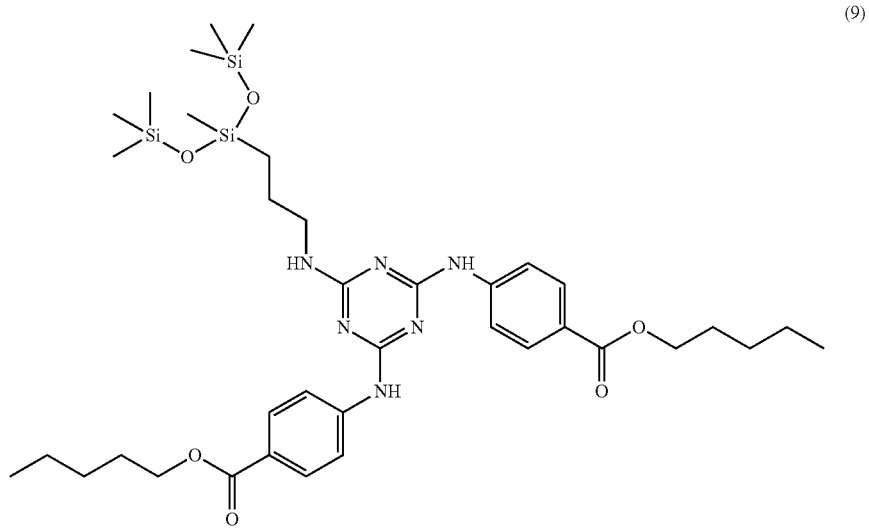 [SMILES: CCCCCOC(=O)c1ccc(Nc2nc(NCCC[Si](C)(O[Si](C)(C)C)O[Si](C)(C)C)nc(Nc3ccc(C(=O)OCCCCC)cc3)n2)cc1]

(9)

n-Pentyl para-aminobenzoate (40 g, 0.0193 mol), 2-butanone (200 ml) and potassium carbonate (13.34 g) dissolved in 116 ml of water are successively introduced into a reactor while bubbling with nitrogen. The mixture is cooled to 0-5° C. and cyanuric chloride (17.8 g, 0.0965 mol), dissolved in 68 ml of 2-butanone, is introduced dropwise over 1 hour 30 minutes. The mixture is heated at 70° C. for 17 hours; the 2,4-bis(n-pentyl 4'-aminobenzoate)-6-chloro-s-triazine formed is not isolated.

8.11 g of sodium bicarbonate are added to the reaction mixture and then the product from the first stage of Example 2a (27 g, 0.00965 mol) is run in dropwise over 1 hour. Heating is maintained at 70° C. for 4 hours. After cooling, the 2 phases are separated and the organic phase is washed with water and dried. The 2-butanone is removed under reduced pressure. The orangey yellow solid obtained is chromatographed on a silica column (eluent: heptane/EtOAc 9:1). The product of Example 10 (3.79 g, yield 51%) is thus obtained in the form of light beige crystals:

Melting point: 94-95° C.,
UV (Ethanol): $\lambda_{max}$=311 nm, $E_{1\%}$=1265.

Example 11

Preparation of 2,4-bis(n-hexyl 4'-aminobenzoate)-6{[1,3,3,3-tetramethyl-1-[(trimethylsilyl)oxy]disiloxanyl]propyl-3-ylamino}-s-triazine (Route 2)

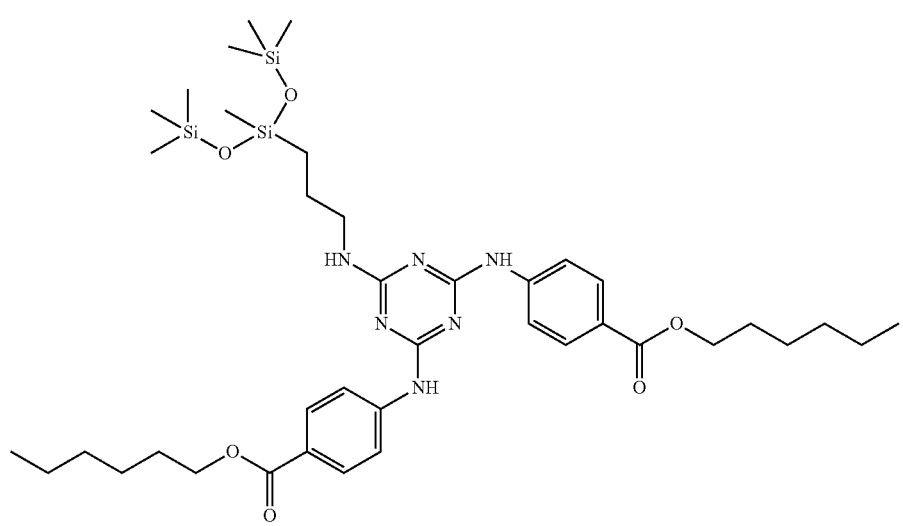

(11)

n-Hexyl para-aminobenzoate (19.32 g, 0.0904 mol) is dissolved in 50 ml of ethyl acetate in a reactor while bubbling with argon. Pyridine (7.3 ml), dissolved in 15 ml of ethyl acetate, is added thereto. The mixture is heated to 70° C. and a solution of the derivative from the first stage of Example 3 (19.32 g, 0.0452 mol) in 50 ml of ethyl acetate is run in dropwise over 30 minutes. The mixture is left at 70° C. for 2 hours. After cooling, the organic phase is washed with a saturated sodium chloride solution and then with water and dried. The paste obtained is chromatographed on a silica column (eluent: heptane/EtOAc 9:1). The clean fractions of the product of Example 11 are thus obtained (12.4 g, yield 34%) in the form of a white powder:

Melting point: 40-41° C.,
UV (Ethanol): $\lambda_{max}$=311 nm, $E_{1\%}$=1371.

Example 12

Preparation of 2,4-bis(cyclohexyl 4'-aminobenzoate)-6-{[1,3,3,3-tetramethyl-1-[(trimethylsilyl)oxy]disiloxanyl]propyl-3-ylamino}-s-triazine (Route 2)

Cyclohexyl para-aminobenzoate (20 g, 0.0912 mol) is dissolved in 50 ml of ethyl acetate in a reactor while bubbling with argon. Pyridine (7.4 ml), dissolved in 15 ml of ethyl acetate, is added thereto. The mixture is heated at 70° C. and a solution of the derivative from the first stage of Example 3 (19.5 g, 0.0456 mol) in 50 ml of ethyl acetate is run in dropwise over 30 minutes. The mixture is left at 70° C. for 2 hours. After cooling, the organic phase is washed with a saturated sodium chloride solution and then with water and dried. The paste obtained is chromatographed on a silica column (eluent: heptane/EtOAc 8:2). The clean fractions of the product of Example 12 are thus obtained (31.8 g, yield 82%) in the form of a beige powder:

Melting point: 74-75° C.,
UV (Ethanol): $\lambda_{max}$=311 nm, $E_{1\%}$=1412.

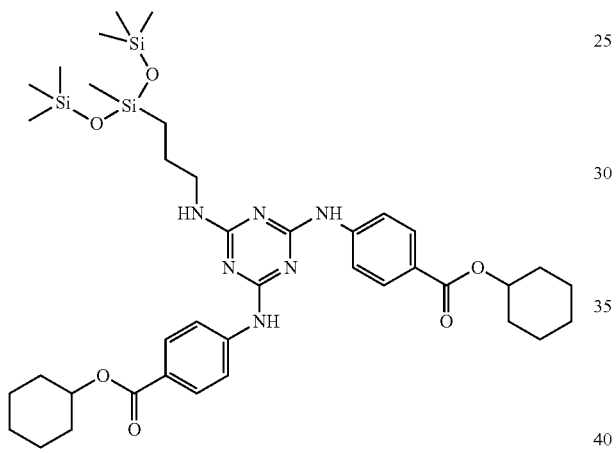

(12)

Example 13

Preparation of 2,4-bis(2-ethylhexyl 4'-aminobenzoate)-6-{[1,3,3,3-tetramethyl-1-[(trimethylsilyl)oxy]disiloxanyl]propyl-3-ylamino}-s-triazine (Route 2)

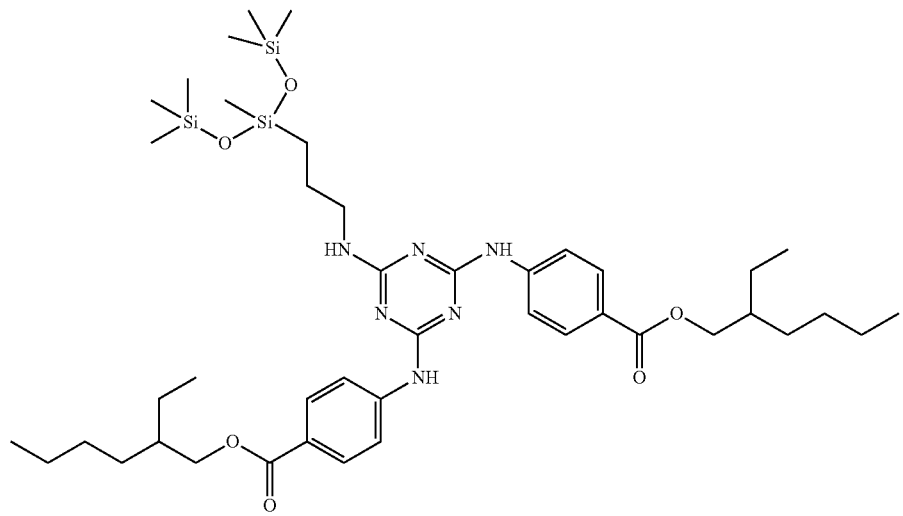

(14)

2-Ethylhexyl para-aminobenzoate (20 g, 0.0802 mol) is dissolved in 50 ml of ethyl acetate in a reactor while bubbling with argon. Pyridine (6.5 ml), dissolved in 15 ml of ethyl acetate, is added thereto. The mixture is heated to 70° C. and a solution of the derivative from the first stage of Example 3 (17.2 g, 0.0401 mol) in 50 ml of ethyl acetate is run in dropwise over 30 minutes. The mixture is left at 70° C. for 2 hours. After cooling, the organic phase is washed with a saturated sodium chloride solution and then with water and dried. The paste obtained is chromatographed on a silica column (eluent: heptane/EtOAc 8:2). The clean fractions of the product of Example 13 are thus obtained (14.4 g, Yield 42%) in the form of a pale brown wax:

UV (Ethanol): $\lambda_{max}$=311 nm, $E_{1\%}$=1450.

Example 14

Preparation of 2,4-bis(2-ethylhexyl 2'-hydroxy-4'-aminobenzoate)-6-{[1,3,3,3-tetramethyl-1-[(trimethylsilyl)oxy]disiloxanyl]propyl-3-ylamino}-s-triazine (Route 2)

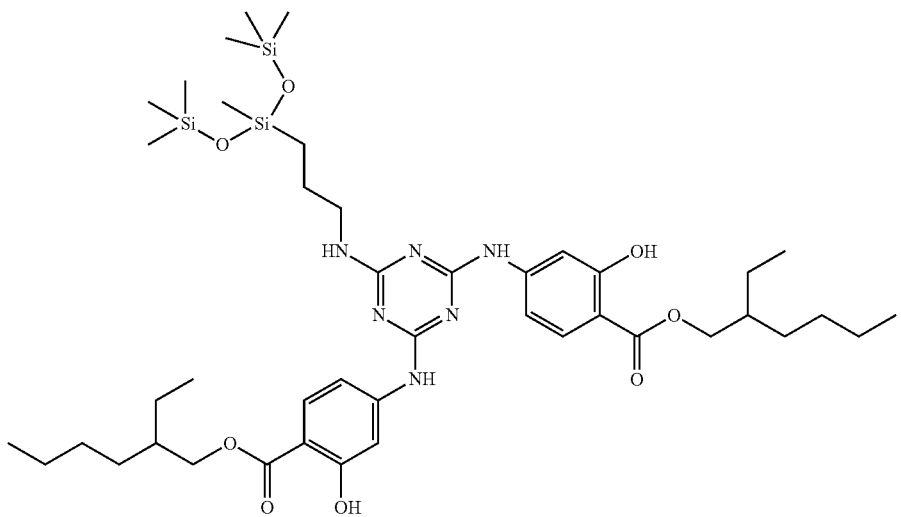

(15)

A mixture of 2-ethylhexyl 2-hydroxy-4-aminobenzoate (1.4 g, 5.57×10$^{-3}$ mol) and the product from the first stage of Example 3 (1.19 g, 2.78×10$^{-3}$ mol) in 10 ml of toluene is heated at reflux for 5 hours while sparging with nitrogen. The mixture is cooled and the solvent is evaporated. The residue is chromatographed on a silica column (eluent: heptane/EtOAc 9:1). 1.58 g of the clean fractions of the derivative of Example 14 are obtained (yield: 64%) in the form of a white paste:

UV (Ethanol): $\lambda_{max}$=300 nm, $E_{1\%}$=480
$\lambda$max=325 nm, $E_{1\%}$=709.

Example 15

Preparation of butyl 4-{[4-{[4-(butoxycarbonyl)phenyl]-amino}-6-({3-[diethoxy(methyl)silyl]propyl}amino)-1,3,5-triazin-2-yl]amino}-benzoate (Route 2)

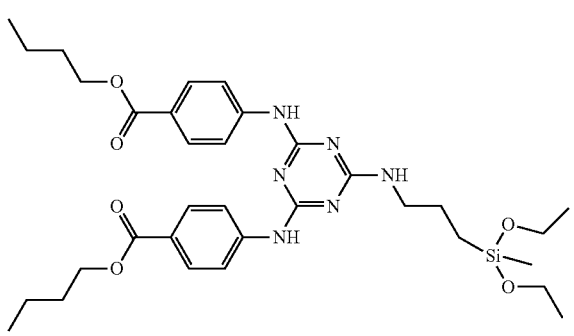

(17)

First Stage

Preparation of 2,4-bis(n-butyl 4'-aminobenzoate)-6-chloro-s-triazine n-Butyl para-aminobenzoate (113.94 g, 0.59 mol) and a solution of potassium carbonate (40.68 g, 0.295 mol) in 50 ml of water are simultaneously added dropwise at 5° C. to a solution of cyanuric chloride (54.36 g, 0.295 mol) in 500 ml of dioxane and 50 ml of water, so that the pH lies between 3 and 6.5. The mixture is maintained at 5° C. for 1 hour 30 minutes. A precipitate is formed in the medium, which corresponds to the monosubstituted s-triazine. The mixture is gradually heated to 70° C. and the second equivalent of potassium carbonate (40.68 g, 0.295 mol) in 50 ml of water is added. Stirring is subsequently maintained at 70° C. for 5 hours. The reaction mixture is cooled and filtered. The precipitate formed is washed with water, superficially dewatered and dried. After recrystallizing from dioxane/water and drying under vacuum, 52.5 g (yield: 36%) of the first recrystallization crop of 2,4-bis(n-butyl 4'-aminobenzoate)-6-chloro-s-triazine are obtained in the form of a white powder.

The heterogeneous mixture of the product from the first stage of the example (20 g, 0.04 mol) and aminopropyldiethoxymethylsilane (15.37 g, 0.08 mol) is gradually heated to 70° C. while sparging with nitrogen. After one hour, the mixture is cooled, dichloromethane is added and the organic phase is washed 3 times with water. After drying the organic phase and evaporating the solvents, followed by recrystallization with heptane, 21 g (yield 80%) of a white solid of the derivative of Example 15 are obtained:

UV (Ethanol): $\lambda_{max}$=311 nm, $E_{1\%}$=1197.

Examples 16 and 17

Preparation of the Derivatives butyl 4-[(4-{[4-(butoxycarbonyl)phenyl]amino}-6-{[3-(1-hydroxy-1,3,3,3-tetramethyldi-siloxanyl)propyl]amino}-1,3,5-triazin-2-yl)amino]benzoate and dibutyl 4,4'-{[6-({3-[dihydroxy(methyl)silyl]propyl}amino)-1,3,5-triazine-2,4-diyl]-diimino}dibenzoate (obtained by acid treatment of the derivative of Example 5)

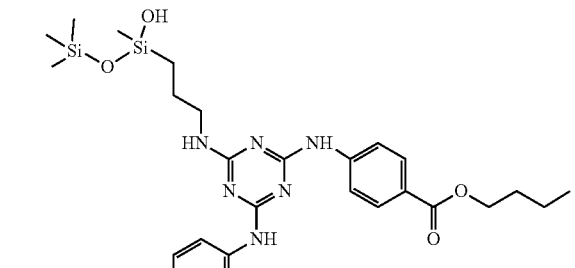

(18)

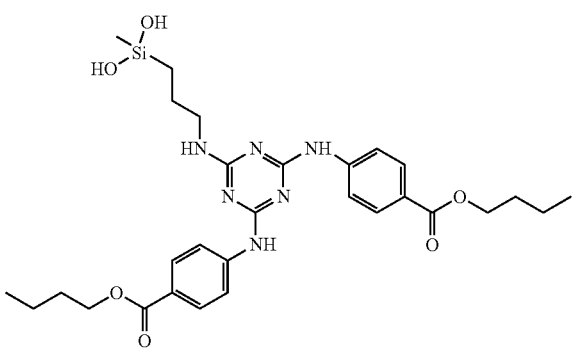

(19)

160 ml of 0.1N hydrochloric acid and 340 ml of the ethanol/isopropanol mixture in the ratio 80:20 are added to the derivative of Example 6 (10 g, 0.013 mol) dissolved in 500 ml of the ethanol/isopropanol mixture in the ratio 80:20. The mixture is left stirring at laboratory temperature for 5 hours. This solution is neutralized with 0.4% sodium hydroxide solution up to a pH of 7. 1 liter of water is added thereto and the solution is lyophilized. The lyophilized batches are combined to give 6.5 g of a light beige powder which comprises, as relative percentages by HPLC, approximately 28% of the derivative of Example 16 and approximately 10% of the derivative of Example 17. This powder was fractionated by centrifugal partition chromatography (with two-phase systems composed of heptane, ethyl acetate, methanol and water in different proportions) to give 0.58 g of the derivative of Example 16 in the form of a white powder:

UV (Ethanol): $\lambda_{max}$=312 nm, $E_{1\%}$=1228 and 0.42 g of the derivative of Example 17 in the form of a white powder.

Example 18

Preparation of butyl 4-({4-{[4-(butoxycarbonyl)-phenyl]amino}-6-[(2-{1,3,3,3-tetramethyl-1-[(trimethylsilyl)oxy]disiloxanyl}-propyl)amino]-1,3,5-triazin-2-yl}amino)benzoate

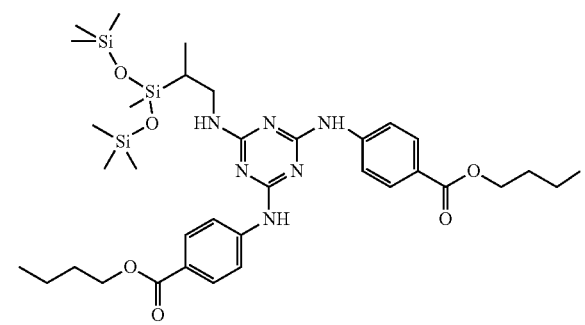

(20)

First Stage

Preparation of 4,6-dichloro-N-(2-{1,3,3,3-tetramethyl-1-[(trimethylsilyl)oxy]disiloxanyl}propyl)-1,3,5-triazin-2-amine A 15/85 mixture of 2-{1,3,3,3-tetramethyl-1-[(trimethylsilyl)oxy]disiloxanyl}-propan-1-amine and of 3-{1,3,3,3-tetramethyl-1-[(trimethylsilyl)oxy]disiloxanyl}-propan-1-amine (49.3 g, 0.176 mol) and a solution of sodium bicarbonate (14.8 g, 0.176 mol) in 210 ml of water are added dropwise at 0° C. to a solution of cyanuric chloride (32.5 g, 0.176 mol) in 180 ml of acetone, so that the pH lies between 4 and 5.8. At the end of the introduction, the pH is 5.3. Stirring is subsequently maintained at 10° C. for 1 hour 30 minutes and is then left at laboratory temperature. The precipitate formed is filtered off, washed with water, superficially dewatered and dried. 72.4 g (yield: 96%) of the isomeric derivatives in the ratio of 15/85 are obtained in the form of a white powder (M.p.: 59° C.). 20 g of this mixture was fractionated by centrifugal partition chromatography (two-phase system: heptane/acetonitrile/water 50:49:1) to give 2.0 g of 4,6-dichloro-N-(2-{1,3,3,3-tetramethyl-1-[(trimethylsilyl)oxy]disiloxanyl}propyl)-1,3,5-triazin-2-amine, used as is in the following stage:

Second Stage

Preparation of the Derivative of Example 18

The preceding product (2 g, 0.0047 mol) is dissolved in 18 ml of toluene. Pyridine (0.8 ml, 0.009 mol) and n-butyl para-aminobenzoate (1.8 g, 0.009 mol) are added thereto. The mixture is heated at 70° C. with stirring for 3 hours. The solution is cooled and poured onto a silica bed and the cake is rinsed with 80 ml of toluene. After evaporating the solvent, the brown-beige solid obtained is crystallized from 30 ml of heptane. 2.2 g (yield 63%) of the derivative of Example 18 are thus obtained in the form of a light beige powder:

Melting point: 149-151° C.,
UV (Ethanol): $\lambda_{max}$=312 nm, $E_{1\%}$=955.

Example 19

Preparation of Compound (21)

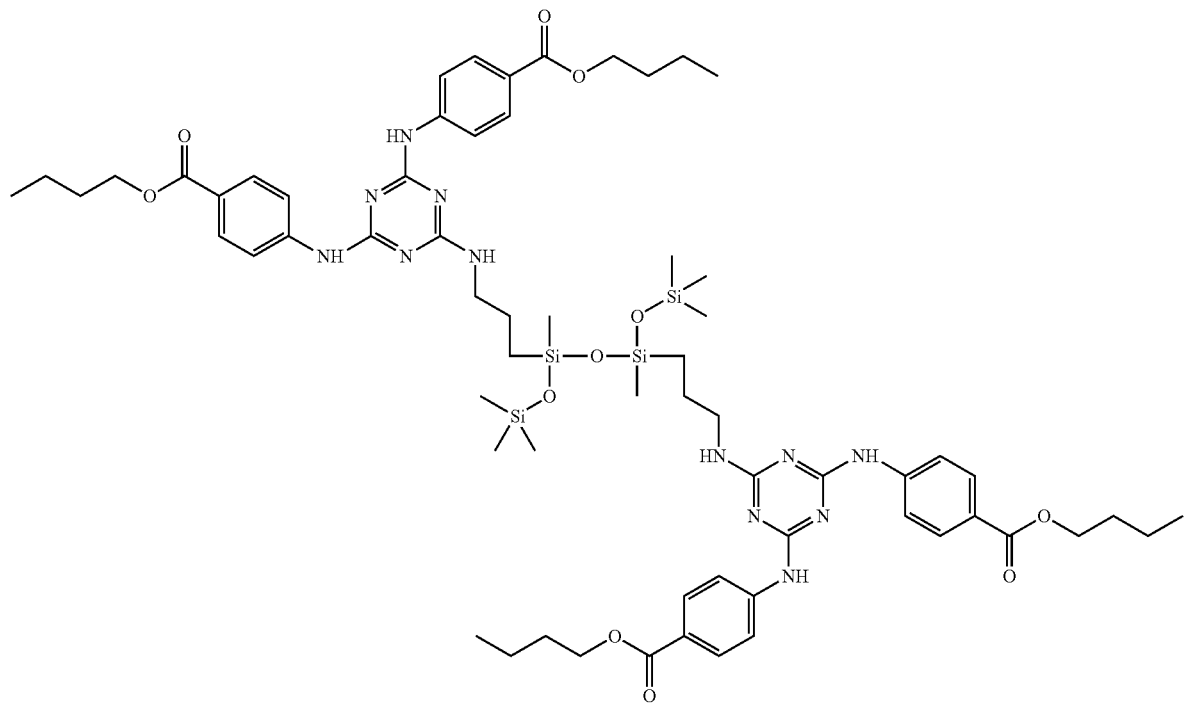

(21)

25 ml of 1N hydrochloric acid are added to the derivative of Example 6 (1 g, 0.0013 mol) dissolved in 50 ml of an ethanol/isopropanol mixture in a ratio 80:20. The mixture is left stirring at laboratory temperature for 4 hours. This solution is neutralized with 35% sodium hydroxide solution up to a pH of 7. The solvents are evaporated under vacuum. 0.8 g of a light beige powder is obtained, which powder comprises, as relative percentage by HPLC, approximately 37% of the derivative of Example 19. This powder was fractionated by centrifugal partition chromatography (with two-phase systems composed of heptane, ethyl acetate, methanol and water) to give 0.18 g of the derivative of Example 19 in the form of a white powder:

UV (Ethanol): $\lambda_{max}$=312 nm, $E_{1\%}$=1109.

Example 20

Preparation of Compound (22)

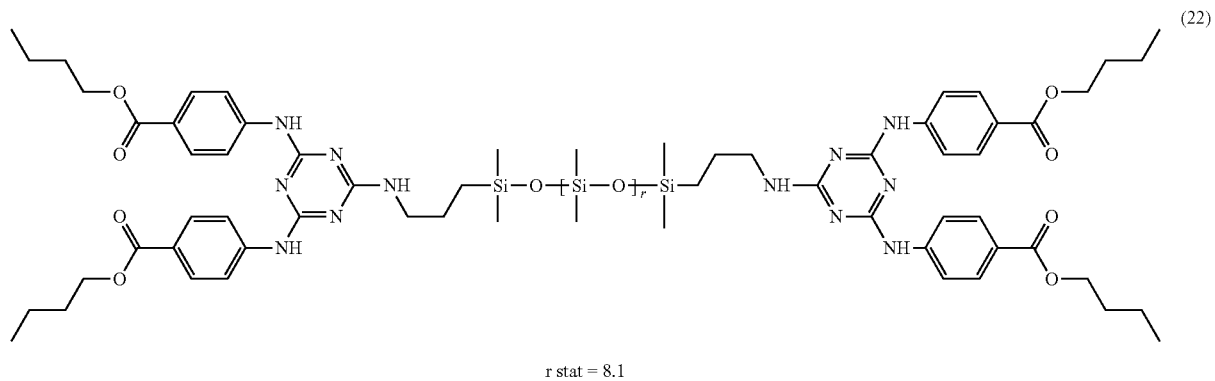

r stat = 8.1

First Stage

Preparation of 2,4-bis(n-butyl 4'-aminobenzoate)-6-chloro-s-triazine n-Butyl para-aminobenzoate (113.94 g, 0.59 mol) and a solution of potassium carbonate (40.68 g, 0.295 mol) in 50 ml of water are simultaneously added dropwise at 5° C. to a solution of cyanuric chloride (54.36 g, 0.295 mol) in 500 ml of dioxane and 50 ml of water, so that the pH lies between 3 and 6.5. The mixture is maintained at 5° C. for 1 hour 30 minutes. A precipitate is formed in the medium, which corresponds to the monosubstituted s-triazine. The mixture is gradually heated to 70° C. and the second equivalent of potassium carbonate (40.68 g, 0.295 mol) in 50 ml of water is added. Stirring is subsequently maintained at 70° C. for 5 hours. The reaction mixture is cooled and filtered. The precipitate formed is washed with water, superficially dewatered and dried. After recrystallizing from dioxane/water and drying under vacuum, 52.5 g (yield: 36%) of the first recrystallization crop of 2,4-bis(n-butyl 4'-aminobenzoate)-6-chloro-s-triazine are obtained in the form of a white powder.

Second Stage

Preparation of the Derivative of Example 20

A mixture of the preceding product (2 g, $4 \times 10^{-3}$ mol), aminopropyl-terminated polydimethylsiloxane (DMS-A-11 from Gelest) (2.13 g, $2 \times 10^{-3}$ mol) and pyridine (0.32 ml, $4 \times 10^{-3}$ mol) in 40 ml of toluene is heated at 70° C. for 5 hours while sparging with nitrogen. The mixture is cooled, dichloromethane is added and the organic phase is washed 3 times with water. After drying the organic phase and evaporating the solvents, a brown oil is obtained. After treatment with carbon black in ethanol under hot conditions and filtering through Celite, 3.3 g (yield: 70%) of the derivative of Example 20 are obtained in the form of a light brown gum:

UV (Ethanol): $\lambda_{max}$=311 nm, $E_{1\%}$=916.

II/Synthesis of Comparative Example (A)

Preparation of 2,4-bis(dodecyl 4'-aminobenzoate)-6-{[1,3,3,3-tetramethyl-1-[(trimethylsilyl)-oxy]disiloxanyl]propyl-3-ylamino}-s-triazine (according to Route 1+2)

(A)

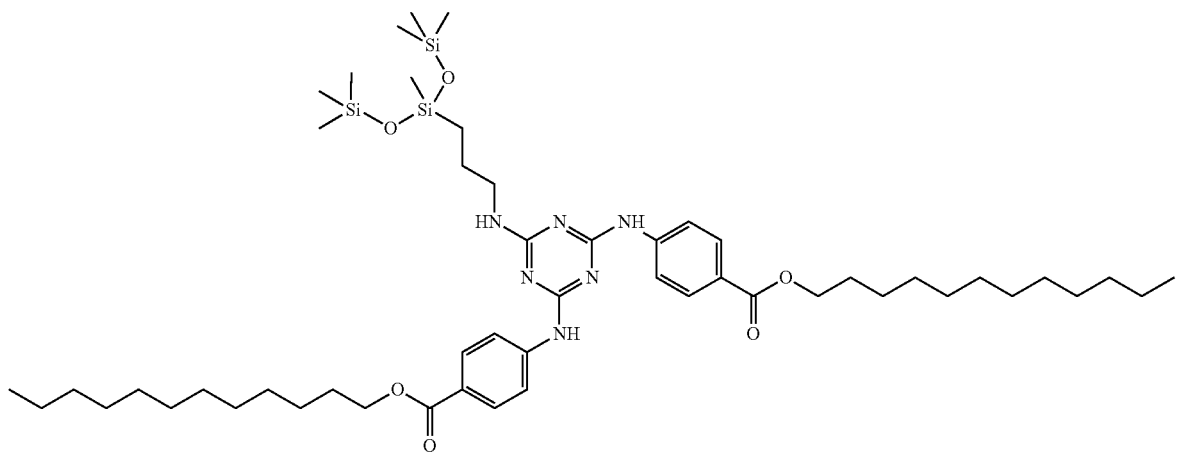

First Stage

Preparation of Dodecyl Para-Aminobenzoate

A mixture of ethyl para-aminobenzoate (33.8 g, mol), n-dodecanol (114.84 ml, mol) and catalyst (dibutyltin diacetate: 544 µl) is heated at 170° C. for 48 hours (the ethanol formed is removed by distillation). The reaction mixture changes from colourless to orange. The mixture is heated at 100° C. for 6 hours under a vacuum of approximately 20 mmHg. The reaction mixture changes from orange to red. The mixture is subsequently heated at 120° C. in order to remove the excess lauryl alcohol.

The brown-red viscous oil is crystallized from methanol. After filtering, washing the cake with cold methanol and drying under vacuum, dodecyl para-aminobenzoate is obtained (52.77 g, yield 84%) in the form of a pale yellow powder and is used as is in the following stage:

Second Stage

Preparation of the Derivative of Comparative Example A 5.3 ml of pyridine in solution in ethyl acetate are added, while flushing with argon and while stirring, to the product of the first stage of Example 2a (20 g, mol) dissolved in ethyl acetate. The mixture is heated to 70° C. and the dodecyl para-aminobenzoate from the preceding stage (14 g, mol) is added portionwise over 10 minutes. The reaction mixture is left at this temperature for 3 hours. The reaction mixture, which is red/black in colour, is cooled and is washed twice with a saturated sodium chloride solution and then with water in suspension in 20 ml of toluene is heated at reflux for 1 hour 30 minutes. The mixture is cooled and hot heptane is added to the resin obtained. After triturating, filtering and drying, 2.3 g (yield: 67%) of the derivative of Comparative Example A are obtained in the form of a pale brown wax:

Melting point: 134-135° C.,

UV (Ethanol): $\lambda_{max}$=311 nm, $E_{1\%}$=838.

III/Formulation Examples

The following composition A (invention) and compositions outside the invention B, C, D and E were prepared:

| Ingredients | Ex. A | Ex. B (*) | Ex. C (*) | Ex. D (*) | Ex. E (*) |
|---|---|---|---|---|---|
| Phase a | | | | | |
| EDTA | 0.1 | 0.1 | 0.1 | 0.1 | 0.1 |
| Monopotassium monocetyl phosphate | 1 | 1 | 1 | 1 | 1 |
| Deionized water | q.s. for 100 | q.s. for 100 | q.s. for 100 | q.s. for 100 | q.s. for 100 |
| Triethanolamine | 0.3 | 0.3 | 0.3 | 0.3 | 0.3 |
| Preserving agents | 1.2 | 1.2 | 1.2 | 1.2 | 1.2 |
| Phase $b_1$ | | | | | |
| $C_{12}$-$C_{15}$ alkyl benzoate | 20 | 20 | 20 | 20 | 20 |
| Preserving agents | 0.25 | 0.25 | 0.25 | 0.25 | 0.25 |
| Stearic acid | 1.5 | 1.5 | 1.5 | 1.5 | 1.5 |
| Glyceryl mono/distearate/polyethyene glycol stearate (100 EO) mixture | 1 | 1 | 1 | 1 | 1 |
| Cetyl alcohol | 0.5 | 0.5 | 0.5 | 0.5 | 0.5 |
| Cetearyl alcohol and cetearyl glucoside | 2 | 2 | 2 | 2 | 2 |
| Dimethicone (350 cSt) | 0.5 | 0.5 | 0.5 | 0.5 | 0.5 |
| Triethanolamine | 0.45 | 0.45 | 0.45 | 0.45 | 0.45 |
| n-Hexyl 2-(4-diethylamino-2-hydroxybenzoyl)-benzoate (Uvinul A+) | 4 | 4 | 4 | 4 | 4 |
| Silicon-comprising s-triazine substituted by two $C_4$-alkylamino-benzoates Compound (5) | 4 | 0 | 0 | 0 | 0 |
| Silicon-comprising s-triazine substituted by two $C_{12}$-alkylamino-benzoates Compound of Comparative Example (A) | 0 | 4 | 0 | 0 | 0 |
| 2-Ethylhexyl α-cyano-β,β-diphenylacrylate | 0 | 0 | 4 | 0 | 0 |
| 2-Ethylhexyl 4-methoxy-cinnamate | 0 | 0 | 0 | 4 | 0 |
| 2,4,6-Tris[p-(2'-ethylhexyl-1'-oxycarbonyl)anilino]-1,3,5-triazine | 0 | 0 | 0 | 0 | 4 |

-continued

| Ingredients | Ex. A | Ex. B (*) | Ex. C (*) | Ex. D (*) | Ex. E (*) |
|---|---|---|---|---|---|
| Phase b$_2$ | | | | | |
| Isohexadecane | 1 | 1 | 1 | 1 | 1 |
| Copolymer of acrylic acid and of C$_{10}$-C$_{30}$ alkyl methacrylate | 0.2 | 0.2 | 0.2 | 0.2 | 0.2 |
| Xanthan gum | 0.2 | 0.2 | 0.2 | 0.2 | 0.2 |
| Cyclopentadimethylsiloxane | 5 | 5 | 5 | 5 | 5 |

These compositions were evaluated according to the following properties: Solubility of the screening agents, Screening efficacy, Photostability.

Emulsion Preparation Method:

The aqueous phase A and the oily phase B1 are prepared by mixing the starting materials, with mechanical stirring, at 80° C.; the solutions obtained are macroscopically homogeneous. The emulsion is prepared by slow introduction of the oily phase into the aqueous phase with stirring using a Moritz homogenizer at a stirring speed of 4000 rpm for 15 minutes. The emulsion obtained is cooled with stirring to 40° C. and then the oily phase B2 is added thereto with gentle stirring. The emulsion obtained is cooled to room temperature, with slow stirring. It is characterized by drops of between 1 μm and 10 μm in size.

Protocol for Evaluating the Solubility of the UV Screening Agents

Preparation of the solutions of UV screening agents: the screening agent and the oil are weighed out in a 10 ml glass flask for a total mixture of 5 g. Dissolution is carried out under hot conditions on a water bath at 80° C. with magnetic stirring. When dissolution is complete (clear solution), the solution is stored at ambient temperature. The appearance of macroscopic crystals is monitored over time.

Protocol for the In Vitro Evaluation of the Screening Efficacy

| | |
|---|---|
| Spreading support: | frosted PMMA |
| Amount after application: | 0.6 mg/cm$^2$ |
| Application: | bare finger |
| Drying time: | 20 minutes at AT, in darkness |
| Number of samples: | 5 applications per formulation |
| | 5 measuring points per application |
| Measurement device: | UV analyser - Labsphere UV 1000S |

Recording of the monochromatic protection factors every nm between 290 and 400 nm Calculation of the SPF according to the method described by B. L. Diffey. et al. in J. Soc. Cosmet. Chem., 40, 127-133 (1989).

| | |
|---|---|
| Source spectrum: | Diffey sun 1989 |
| Action spectrum: | Erythema CIE 1987 |

Protocol for the Evaluation of the Photostability of the Screening Agents

The photostability of the UV screening agent is evaluated by HPLC assaying of the residual screening agent after exposure of a thin film of formulation to the Suntest at a UV dose equivalent to 1H radiometric UV-A.

| | |
|---|---|
| Spreading support: | frosted PMMA |
| Amount after application: | 2 mg/cm$^2$ |
| Number of samples: | 4 plates/formulation of exposed to UV radiation |

4 control plates/formulation are stored in an oven at 37° C.

| | |
|---|---|
| Solar simulator: | Suntest Heraeus - Atlas |
| | UV-A flux = 8.23 × 10$^{-3}$ W/cm$^2$ |
| | UV-B flux = 1.42 × 10$^{-3}$ W/cm$^2$ |
| | Exposure time = 44 minutes |

The UV-A and UV-B irradiations of the Suntest are measured radiometrically.

| | |
|---|---|
| Extraction of the cream film: | Ethanol + ultrasound |
| Assaying of the residual screening agent: | HPLC |

Calculation of the % of photostability relative to the unexposed samples.

Results:

| Examples | In vitro SPF | Solubility | Residual % of lipophilic 2-hydroxybenzophenone (Uvinul A+) (n-Hexyl 2-(4-diethylamino-2-hydroxybenzoyl)-benzoate) | Residual % of UV-B screening agent |
|---|---|---|---|---|
| Example A (invention) | ++ | YES | >90% | >90% |
| Example B | -- | YES | >90% | >90% |
| Example C | -- | YES | >90% | >90% |
| Example D | ++ | YES | >90% | Loss |
| Example E | ++ | NO | >90% | >90% |

These results show that only the combination of a UV-A screening agent of 2-hydroxybenzophenone type (Uvinul A+) (n-Hexyl 2-(4-diethylamino-2-hydroxybenzoyl)-benzoate) and of a UV-B screening agent chosen from the silicon-comprising s-triazines substituted by two aminobenzoate groups of formula (III) makes it possible to obtain a screening system of high efficacy, which is easy to employ in cosmetic compositions due to its good solubility and which is photostable. For the combinations based on other UV-B screening agents, such as silicon-comprising s-triazine substituted by two C$_{12}$ alkyl aminobenzoate groups, 2-ethylhexyl α-cyano-β,β-diphenylacrylate, 2-ethylhexyl 4-methoxycinnamate or 2,4,6-tris[p-(2'-ethylhexyl-1'-oxycarbonyl)anilino]-1,3,5-triazine, the performances in terms of screening efficacy, of solubility or of photostability are inferior to those of the combination of the invention.

Formulation Examples 1 to 6

| Chemical name | Ex. 1 | Ex. 2 | Ex. 3 (*) | Ex. 4 (*) | Ex. 5 (*) | Ex. 6 (*) |
|---|---|---|---|---|---|---|
| Phase a | | | | | | |
| Silicon-comprising s-triazine substituted by two aminobenzoate groups Compound (5) | 2 | 2 | — | — | — | — |
| n-Hexyl 2-(4-diethyl-amino-2-hydroxy-benzoyl)benzoate | 1.5 | 2.5 | 2.5 | 2.5 | 2.5 | 2.5 |
| Butyl Methoxy Dibenzoylmethane | 2 | 2 | 2 | 2 | 2 | 2 |
| Silicon-comprising s-triazine substituted by two aminobenzoate groups Compound (A) | — | 2 | — | — | — | — |
| 2-Ethylhexyl α-cyano-β,β-diphenylacrylate | — | — | — | 2 | — | — |
| 2-Ethylhexyl 4-methoxycinnamate | — | — | — | — | 2 | — |
| 2,4,6-Tris[p-(2'-ethyl-hexyl-1'-oxycarbonyl)-anilino]-1,3,5-triazine | — | — | — | — | — | 2 |
| $C_{12}$-$C_{15}$ Alkyl benzoate | 5 | 5 | 5 | 5 | 5 | 5 |
| Phenethyl benzoate (and) benzoic acid | 10 | 10 | 10 | 10 | 10 | 10 |
| Cetyl alcohol | 0.5 | 0.5 | 0.5 | 0.5 | 0.5 | 0.5 |
| Stearic acid | 1.5 | 1.5 | 1.5 | 1.5 | 1.5 | 1.5 |
| Glyceryl monostearate/PEG (100 EO) stearate mixture | 1 | 1 | 1 | 1 | 1 | 1 |
| Mixture of cetylstearyl glucoside and of cetyl and stearyl alcohols | 2 | 2 | 2 | 2 | 2 | 2 |
| Dimethicone | 0.50 | 0.50 | 0.50 | 0.50 | 0.50 | 0.50 |
| Triethanolamine | 0.45 | 0.45 | 0.45 | 0.45 | 0.45 | 0.45 |
| Preserving agent | 1 | 1 | 1 | 1 | 1 | 1 |
| Phase b | | | | | | |
| Glycerol | 5 | 5 | 5 | 5 | 5 | 5 |
| Complexing agent | 0.1 | 0.1 | 0.1 | 0.1 | 0.1 | 0.1 |
| Monocetyl phosphate | 1 | 1 | 1 | 1 | 1 | 1 |
| Water | q.s. for 100 g | q.s. for 100 g | q.s. for 100 g | q.s. for 100 g | q.s. for 100 g | q.s. for 100 g |
| Phase c | | | | | | |
| Xanthan gum | 0.2 | 0.2 | 0.2 | 0.2 | 0.2 | 0.2 |
| Acrylic acid/stearyl methacrylate copolymer | 0.2 | 0.2 | 0.2 | 0.2 | 0.2 | 0.2 |
| Isohexadecane | 1 | 1 | 1 | 1 | 1 | 1 |
| Cyclopentasiloxane | | | 1 | 1 | 1 | 1 |
| Phase d | | | | | | |
| Triethanolamine | q.s. pH | q.s. pH | q.s. pH | q.s. pH | q.s. pH | q.s. pH |

Procedure

Fatty phase a is heated to 70° C. Aqueous phase b is heated in the final beaker. Phase c is prepared: dispersion of the powders in the oil. The fatty phase is emulsified in the aqueous phase with stirring using a rotor-stator. Phase c is introduced with faster stirring and then the mixture is left under slow stirring until it has returned to ambient temperature. The mixture is neutralized with phase d and packaged.

The invention claimed is:

1. A composition comprising:
   (i) 0.01 to 10% by weight of n-hexyl 2-(4-diethylamino-2-hydroxybenzoyl)benzoate of formula (a):

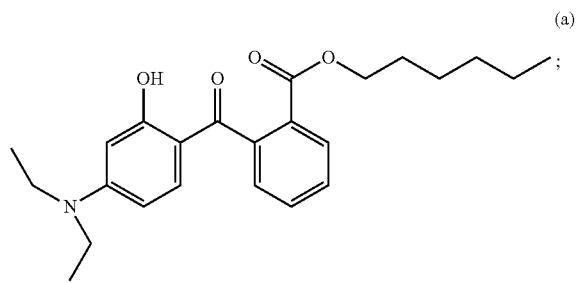 [SMILES: CCCCCCOC(=O)c1ccccc1C(=O)c1ccc(N(CC)CC)cc1O]

and
   (ii) 0.01 to 20% by weight of 2,4-bis(n-butyl 4'-aminobenzoate)-6-[(3-{1,3,3,3-tetramethyl-1-[(trimethylsilyl)oxy]disiloxanyl}propyl)amino]-s-triazine of formula (5):

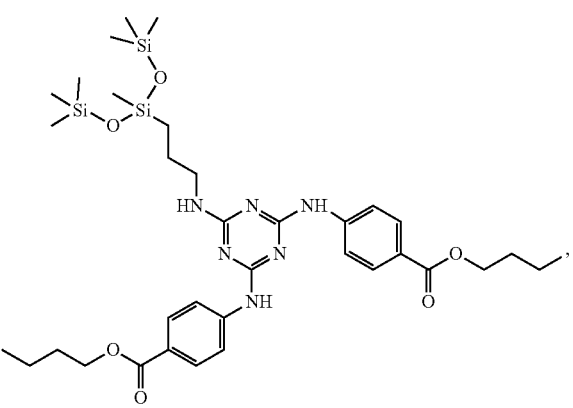

wherein the composition does not include a dibenzoylmethane derivative.

2. The composition of claim 1, further comprising an organic UV screening agent selected from the group consisting of:
   ethylhexyl methoxycinnamate,
   homosalate,
   ethylhexyl salicylate,
   octocrylene,
   phenylbenzimidazole sulphonic acid,
   4-Methylbenzylidene camphor,
   ethylhexyl triazone,
   bis-ethylhexyloxyphenol methoxyphenyl triazine,
   diethylhexyl butamido triazone,
   2,4,6-Tris(biphenyl-4-yl)-1,3,5-triazine,
   2,4,6-Tris(dineopentyl 4'-aminobenzalmalonate)-s-triazine,
   2,4,6-Tris(diisobutyl 4'-aminobenzalmalonate)-s-triazine,
   2,4-Bis(dineopentyl 4'-aminobenzalmalonate)-6-(n-butyl 4'-aminobenzoate)-s-triazine,
   methylene bis-benzotriazolyl tetramethylbutylphenol,
   polysilicone-15,
   dineopentyl 4'-methoxybenzalmalonate, 1,1-Dicarboxy(2,2'-dimethylpropyl)-4,4-diphenylbutadiene, 2,4-Bis[4-[5-(1,1-dimethylpropyl)benzoxazol-2-yl]phenylimino]-6-(2-ethylhexyl)imino-1,3,5-triazine, and a mixture thereof.

3. The composition of claim 1, further comprising monopotassium monocetyl phosphate.

4. The composition of claim 1, further comprising water.

5. The composition of claim 1, further comprising triethanolamine.

6. The composition of claim 1, further comprising a preserving agent.

7. The composition of claim 1, further comprising $C_{12}$-$C_{15}$ alkyl benzoate.

8. The composition of claim 1, further comprising a PEG 100 stearate/glyceryl stearate mixture.

9. The composition of claim 1, further comprising dimethicone.

10. The composition of claim 1, in the form of an emulsion.

11. The composition of claim 1, further comprising isohexadecane.

12. The composition of claim 1, further comprising a copolymer of acrylic acid and of $C_{10}$-$C_{30}$ alkyl methacrylate.

13. The composition of claim 1, further comprising cyclopentadimethylsiloxane.

14. The composition of claim 1 in the form of an emulsion and further comprising a preserving agent, water, and dimethicone.

15. The composition of claim 1, further comprising isohexadecane.

16. The composition of claim 1, further comprising a copolymer of acrylic acid and of $C_{10}$-$C_{30}$ alkyl methacrylate.

17. A method for protecting the skin and/or keratin materials against UV radiation comprising applying the composition of claim 1 to the skin and/or keratin materials.

* * * * *